(12) United States Patent
Yost et al.

(10) Patent No.: US 11,804,390 B2
(45) Date of Patent: **\*Oct. 31, 2023**

(54) SYSTEMS FOR INTEGRATED DECOMPOSITION AND SCANNING OF A SEMICONDUCTING WAFER

(71) Applicant: Elemental Scientific, Inc., Omaha, NE (US)

(72) Inventors: Tyler Yost, Omaha, NE (US); Daniel R. Wiederin, Omaha, NE (US); Beau Marth, Omaha, NE (US); Jared Kaser, Lincoln, NE (US); Jonathan Hein, Elkhorn, NE (US); Jae Seok Lee, Omaha, NE (US); Jae Min Kim, Omaha, NE (US); Stephen H. Sudyka, Omaha, NE (US)

(73) Assignee: Elemental Scientific, Inc., Omaha, NE (US)

( \* ) Notice: Subject to any disclaimer, the term of this patent is extended or adjusted under 35 U.S.C. 154(b) by 0 days.

This patent is subject to a terminal disclaimer.

(21) Appl. No.: 17/562,411

(22) Filed: Dec. 27, 2021

(65) Prior Publication Data
US 2022/0189794 A1    Jun. 16, 2022

Related U.S. Application Data

(63) Continuation of application No. 16/200,038, filed on Nov. 26, 2018, now Pat. No. 11,244,841.

(Continued)

(51) Int. Cl.
*H01L 21/67*    (2006.01)
*H01L 21/66*    (2006.01)
(Continued)

(52) U.S. Cl.
CPC ......... *H01L 21/6719* (2013.01); *G01N 21/73* (2013.01); *H01J 49/105* (2013.01);
(Continued)

(58) Field of Classification Search
CPC .................................................. H01L 21/6719
(Continued)

(56) References Cited

U.S. PATENT DOCUMENTS 4,161,356 A    7/1979    Giffin
4,609,575 A    9/1986    Burkman
(Continued)

FOREIGN PATENT DOCUMENTS

CN    1501173 A    6/2004
CN    103801466 A    5/2014
(Continued)

OTHER PUBLICATIONS

Office Action for Taiwan Application No. 109114438, dated Jul. 20, 2022.
(Continued)

*Primary Examiner* — Walter L Lindsay, Jr.
*Assistant Examiner* — Philip T Fadul
(74) *Attorney, Agent, or Firm* — Kevin E. West; Advent, LLP

(57) ABSTRACT

Systems and methods are described for integrated decomposition and scanning of a semiconducting wafer, where a single chamber is utilized for decomposition and scanning of the wafer of interest.

20 Claims, 22 Drawing Sheets

Related U.S. Application Data

(60) Provisional application No. 62/676,234, filed on May 24, 2018, provisional application No. 62/593,665, filed on Dec. 1, 2017.

(51) Int. Cl.
*H01L 21/677* (2006.01)
*H01J 49/10* (2006.01)
*G01N 21/73* (2006.01)
*H01J 49/00* (2006.01)
*G01N 33/00* (2006.01)

(52) U.S. Cl.
CPC ...... *H01L 21/6708* (2013.01); *H01L 21/6715* (2013.01); *H01L 21/67051* (2013.01); *H01L 21/67126* (2013.01); *H01L 21/67259* (2013.01); *H01L 21/67748* (2013.01); *H01L 21/67772* (2013.01); *H01L 22/14* (2013.01); *H01L 22/34* (2013.01); *G01N 2033/0095* (2013.01); *H01J 49/00* (2013.01); *H01L 22/12* (2013.01)

(58) Field of Classification Search
USPC ........................................................ 73/31.07
See application file for complete search history.

(56) References Cited

U.S. PATENT DOCUMENTS

| | | | |
|---|---|---|---|
| 6,053,984 | A | 4/2000 | Petvai et al. |
| 6,182,675 | B1 | 2/2001 | Naka et al. |
| 6,210,481 | B1 | 4/2001 | Sakai et al. |
| 6,921,466 | B2 | 7/2005 | Hongo et al. |
| 6,937,691 | B2 | 8/2005 | Yamagami et al. |
| 6,939,410 | B2 | 9/2005 | Ko et al. |
| 6,952,253 | B2 | 10/2005 | Lof et al. |
| 7,741,583 | B2 | 6/2010 | Winkler et al. |
| 7,938,129 | B2 | 5/2011 | Hiroe et al. |
| 8,926,762 | B2 | 1/2015 | Chien et al. |
| 8,926,788 | B2 | 1/2015 | Hohenwarter |
| 9,378,940 | B2 | 6/2016 | Kawano et al. |
| 11,049,741 | B2 | 6/2021 | Yost et al. |
| 11,244,841 | B2 * | 2/2022 | Yost .................. H01L 21/6715 |
| 2002/0134406 | A1 | 9/2002 | Heo et al. |
| 2004/0115567 | A1* | 6/2004 | Mandal .................. G03F 7/3021 430/327 |
| 2004/0131783 | A1 | 7/2004 | Lee |
| 2004/0191140 | A1 | 9/2004 | Wen |
| 2004/0211762 | A1 | 10/2004 | Sekiya |
| 2004/0247787 | A1 | 12/2004 | Mackie et al. |
| 2004/0261817 | A1 | 12/2004 | Araki et al. |
| 2005/0028840 | A1 | 2/2005 | Lee et al. |
| 2005/0126605 | A1 | 6/2005 | Yassour et al. |
| 2006/0027763 | A1 | 2/2006 | Deak, IV |
| 2007/0166655 | A1 | 7/2007 | Ooshima et al. |
| 2007/0175500 | A1 | 8/2007 | Hohenwarter |
| 2007/0221253 | A1 | 9/2007 | Nishikido |
| 2008/0090341 | A1 | 4/2008 | Tanaka et al. |
| 2009/0250569 | A1 | 10/2009 | Kim et al. |
| 2009/0317981 | A1 | 12/2009 | Lee |
| 2010/0051943 | A1 | 3/2010 | Fujii |
| 2011/0226626 | A1 | 9/2011 | Choi et al. |
| 2012/0103522 | A1 | 5/2012 | Hohenwarter |
| 2014/0154871 | A1 | 6/2014 | Hwang et al. |
| 2014/0216585 | A1* | 8/2014 | Tjandra ............. H01L 21/67017 137/896 |
| 2015/0107634 | A1 | 4/2015 | Chang Chien et al. |
| 2015/0179393 | A1 | 6/2015 | Colvin et al. |
| 2017/0072378 | A1 | 3/2017 | Wu et al. |
| 2017/0160233 | A1 | 6/2017 | Kawabata et al. |
| 2017/0232784 | A1 | 8/2017 | Tan |
| 2017/0294332 | A1 | 10/2017 | LaBrie et al. |
| 2019/0001334 | A1 | 1/2019 | Kaigala et al. |
| 2019/0013248 | A1 | 1/2019 | Kawabata et al. |

FOREIGN PATENT DOCUMENTS

| | | |
|---|---|---|
| CN | 102974563 B | 1/2016 |
| CN | 206043779 U | 3/2017 |
| CN | 104347452 B | 10/2017 |
| CN | 109791097 A | 5/2019 |
| EP | 1273907 A1 | 1/2003 |
| JP | H1092784 A | 4/1998 |
| JP | H11329955 A | 11/1999 |
| JP | 2003188070 A | 7/2003 |
| JP | 2003203851 A | 7/2003 |
| JP | 2009059825 A | 3/2009 |
| JP | 2011095016 A | 5/2011 |
| JP | 5234847 B2 | 7/2013 |
| JP | 2013544025 A | 12/2013 |
| JP | 2017053806 A | 3/2017 |
| KR | 101210910 B1 | 12/2012 |
| KR | 101918784 B1 | 11/2018 |
| TW | 201234441 A | 8/2012 |
| TW | 201437746 A | 10/2014 |
| TW | 201507043 A | 2/2015 |
| TW | 201511318 A | 3/2015 |
| TW | 201533539 A | 9/2015 |
| TW | 201541512 A | 11/2015 |
| TW | 201613016 A | 4/2016 |
| TW | 201619703 A | 6/2016 |
| TW | 201636735 A | 10/2016 |
| TW | 201638674 A | 11/2016 |
| TW | 201724312 A | 7/2017 |
| WO | 2005036623 A1 | 4/2005 |
| WO | 2017149833 A1 | 9/2017 |

OTHER PUBLICATIONS

Office Action in Taiwan for Application No. 109114438, dated Jan. 30, 2023.
Office Action in Taiwan for Application No. 111129907, dated Feb. 13, 2023.
Office Action for Chinese Application No. 201811466998.9, dated Aug. 26, 2021.
Office Action for Taiwan Application No. 107142937, dated Mar. 4, 2020.
Office Action for Taiwan Application No. 109103919, dated Oct. 21, 2021.
Office Action for Taiwan Patent Application No. 107143022, dated Aug. 19, 2019.
Office Action for Taiwan Patent Application No. 109114438, dated Mar. 15, 2021.
Office Action from Taiwan Application No. 109103919, dated Jun. 2, 2021.
Office Action from Taiwan Application No. 109103919, dated Nov. 10, 2020.
PCT International Search Report and Written Opinion forPCT/US2021/026839, dated Jul. 26, 2021.
Search Report for Taiwan Patent Application No. 107142936, dated Nov. 4, 2019.
Office Action in Korea for Patent Application No. 10-2018-0152279, dated May 18, 2023.
Office Action in Korea for Patent Application No. 10-2018-0152284, dated May 18, 2023.
Office Action in Korea for Patent Application No. 10-2018-0152296, dated May 18, 2023.
Office Action in Japan for Application No. 2018-225023, dated Dec. 6, 2022.
Office Action in Japan for Application No. 2018-225026, dated Nov. 8, 2022.
Office Action in Japan for Application No. 2018-225034, dated Oct. 25, 2022.
Notification of Reasons for Refusal for Japanese Application No. 2018-225023, dated Jun. 6, 2023.

* cited by examiner

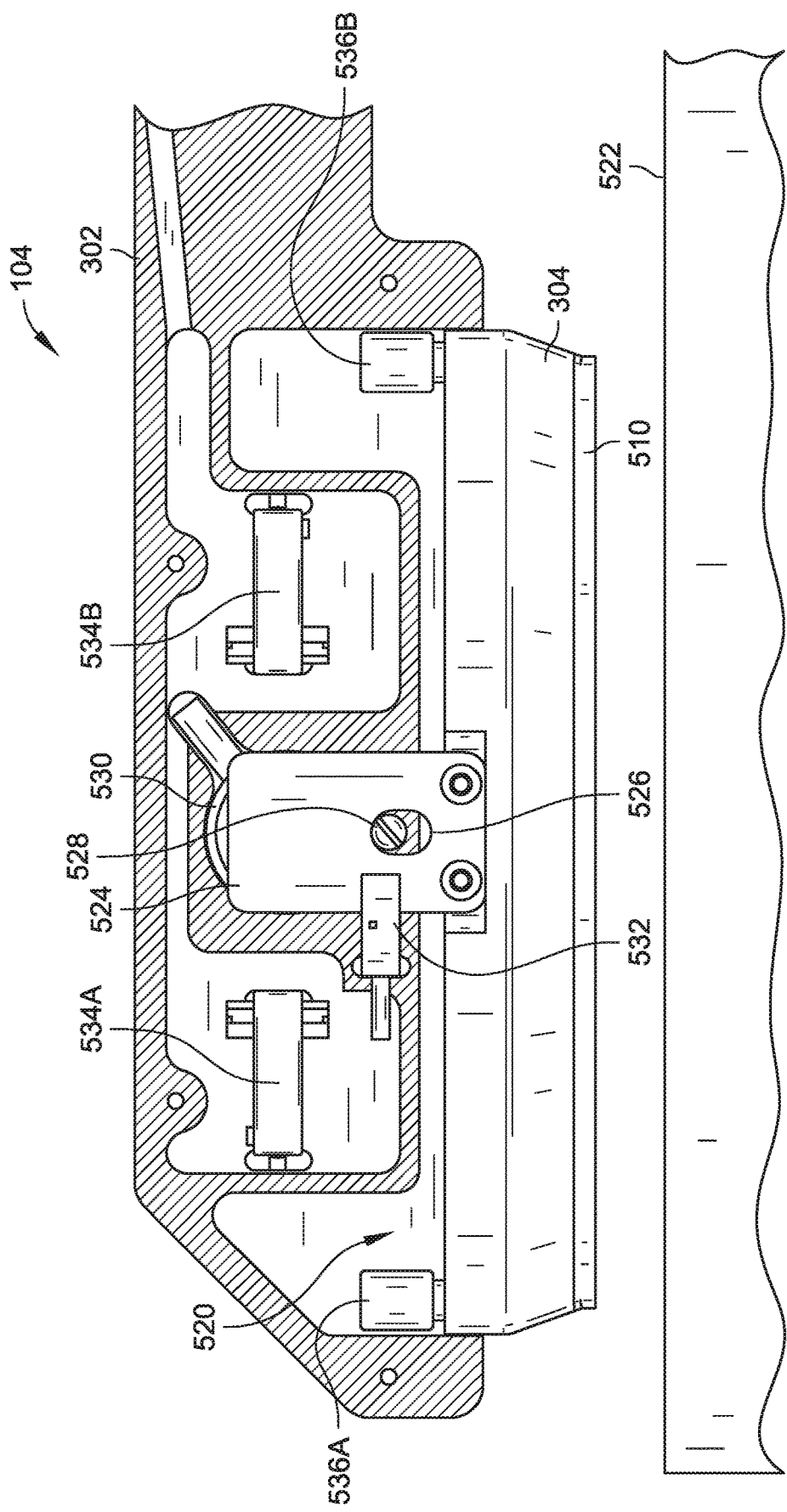

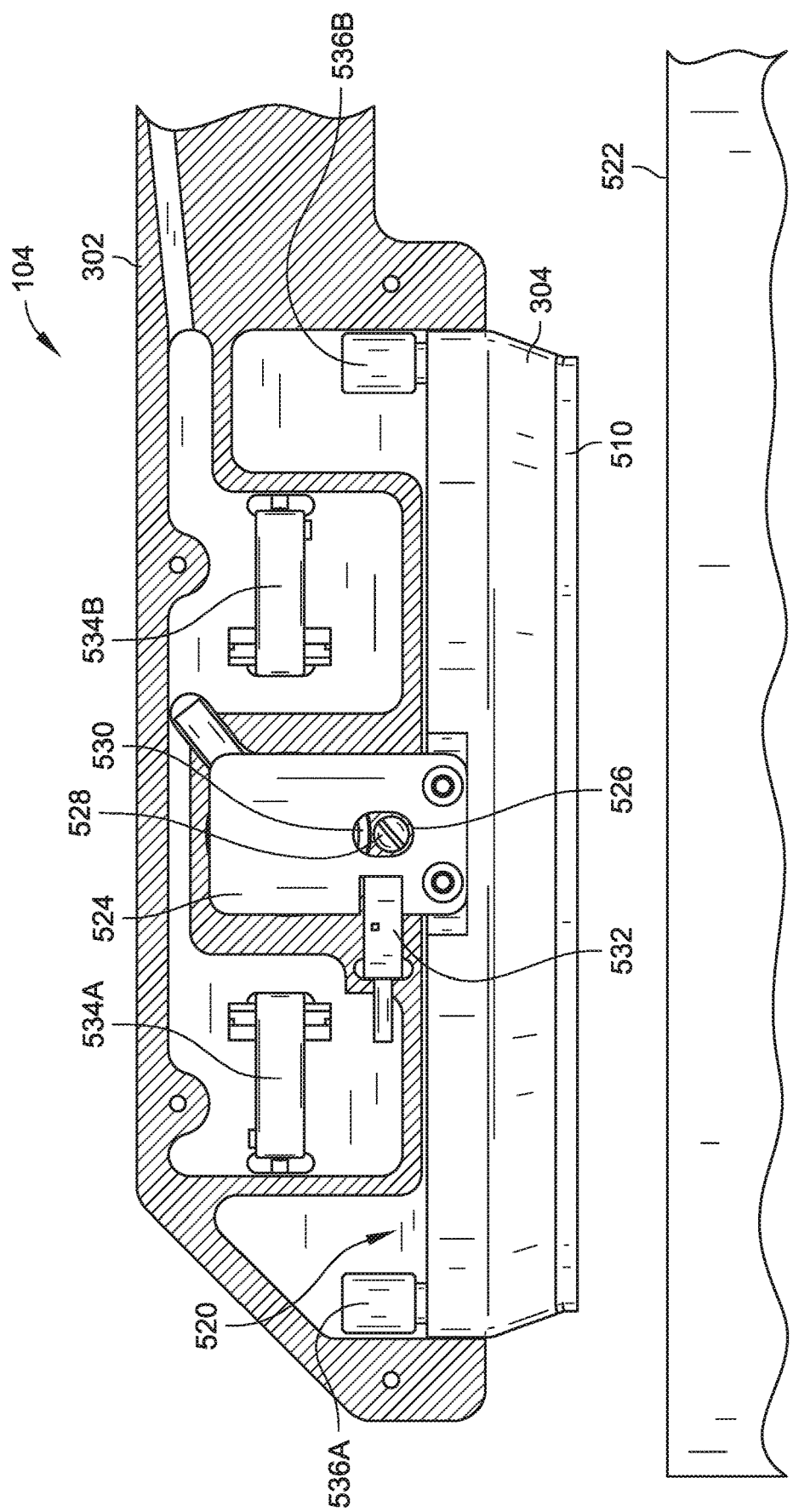

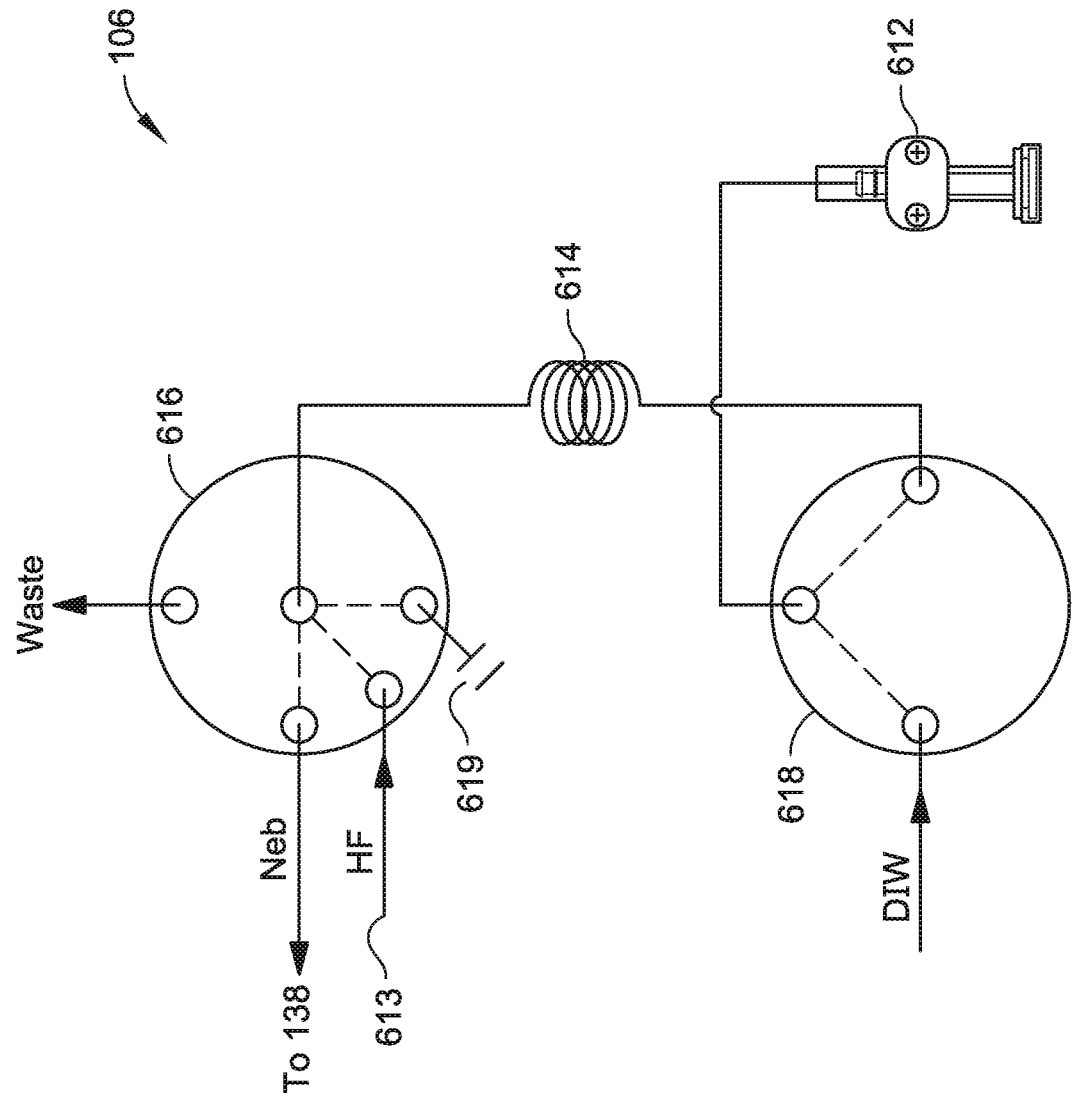

SYSTEMS FOR INTEGRATED DECOMPOSITION AND SCANNING OF A SEMICONDUCTING WAFER

CROSS-REFERENCE TO RELATED APPLICATIONS

The present application is a continuation under 35 U.S.C. § 120 of U.S. patent application Ser. No. 16/200,038, filed Nov. 26, 2018, and titled "SYSTEMS FOR INTEGRATED DECOMPOSITION AND SCANNING OF A SEMICONDUCTING WAFER", which in turn claims the benefit of 35 U.S.C. § 119(e) of U.S. Provisional Application Ser. No. 62/593,665, filed Dec. 1, 2017, and titled "VAPOR PHASE DECOMPOSITION SYSTEM WITH CHAMBER FOR INTEGRATED DECOMPOSITION AND SCANNING" and of U.S. Provisional Application Ser. No. 62/676,234, filed May 24, 2018, and titled "SEMICONDUCTOR WAFER DECOMPOSITION AND SCANNING SYSTEM." U.S. Provisional Application Ser. Nos. 62/593,665 and 62/676,234 and U.S. patent application Ser. No. 16/200,038 are herein incorporated by reference in their entireties.

BACKGROUND

Inductively Coupled Plasma (ICP) spectrometry is an analysis technique commonly used for the determination of trace element concentrations and isotope ratios in liquid samples. ICP spectrometry employs electromagnetically generated partially ionized argon plasma which reaches a temperature of approximately 7,000K. When a sample is introduced to the plasma, the high temperature causes sample atoms to become ionized or emit light. Since each chemical element produces a characteristic mass or emission spectrum, measuring the spectra of the emitted mass or light allows the determination of the elemental composition of the original sample.

Sample introduction systems may be employed to introduce the liquid samples into the ICP spectrometry instrumentation (e.g., an Inductively Coupled Plasma Mass Spectrometer (ICP/ICP-MS), an Inductively Coupled Plasma Atomic Emission Spectrometer (ICP-AES), or the like) for analysis. For example, a sample introduction system may transport an aliquot of sample to a nebulizer that converts the aliquot into a polydisperse aerosol suitable for ionization in plasma by the ICP spectrometry instrumentation. The aerosol generated by the nebulizer is then sorted in a spray chamber to remove the larger aerosol particles. Upon leaving the spray chamber, the aerosol is introduced into the plasma by a plasma torch assembly of the ICP-MS or ICP-AES instruments for analysis.

SUMMARY

Systems and methods are described for integrated decomposition and scanning of a semiconducting wafer, where a single chamber is utilized for decomposition and scanning of the wafer of interest. A chamber embodiment includes, but is not limited to, a chamber body defining an interior region and a first aperture at a top portion of the chamber to receive a semiconducting wafer into the interior region of the chamber body; a ledge projecting into the interior region at an intermediate portion of the chamber body between the top portion of the chamber body and a bottom portion of the chamber body, the ledge defining a second aperture within the interior region at the intermediate portion; a wafer support configured to hold at least a portion of the semiconducting wafer, the wafer support positionable between at least a first position adjacent the first aperture and a second position adjacent the second aperture within the interior region of the chamber body; a motor system operably coupled with the wafer support, the motor system configured to control a vertical position of the wafer support with respect to the chamber body at least to the first position for access to the semiconducting wafer by a scanning nozzle and the second position for decomposition of a surface of the semiconducting wafer; and a nebulizer positioned between the first aperture and the second aperture, the nebulizer configured to spray a decomposition fluid onto the surface of the semiconducting wafer when the wafer support is positioned at the second position by the motor system.

A nozzle system embodiment includes, but is not limited to, a nozzle including a nozzle body defining an inlet port in fluid communication with a first nozzle port, and defining a second nozzle port in fluid communication with an outlet port, the nozzle body configured to receive a fluid through the inlet port and direct the fluid through the first nozzle port to introduce the fluid to a surface of a semiconducting wafer, the nozzle body configured to remove the fluid from the surface of the semiconducting wafer via the second nozzle port and direct the fluid from the second nozzle port through the outlet port, and a nozzle hood extending from the nozzle body adjacent the first nozzle port and the second nozzle port and defining a channel disposed between the first nozzle port and the second nozzle port, the nozzle hood configured to direct the fluid from the first nozzle port to the second nozzle port along the surface of the semiconducting wafer; and a nozzle housing including a housing body defining an interior portion and an aperture through which at least a portion of the nozzle can pass when transitioning between an extended position and a retracted position.

A method embodiment includes, but is not limited to, spraying a decomposition fluid onto a surface of a semiconducting wafer with a nebulizer; positioning a nozzle above the surface of the semiconducting wafer following spraying of the decomposition fluid onto the surface of the semiconducting wafer with the nebulizer; introducing a scan fluid to an inlet port of the nozzle and directing a stream of the scan fluid onto the surface of the semiconducting wafer via a first nozzle port; directing the stream of the scan fluid through an elongated channel of the nozzle along the surface of the semiconducting wafer toward a second nozzle port of the nozzle; and removing the stream of the scan fluid from the surface of the semiconducting wafer via the second nozzle port in fluid communication with an outlet port of the nozzle.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

FIG. 8A is a partial cross-sectional view of a nozzle mount assembly for a system for integrated decomposition and scanning of a semiconducting wafer, in accordance with an embodiment of this disclosure.

FIG. 8C is a partial cross-sectional view of the nozzle mount assembly of FIG. 8A lifted from the surface and leveled.

FIG. 10 is a schematic of a nebulizer fluid handling system for a semiconductor wafer decomposition and scanning system, in accordance with an embodiment of this disclosure.

DETAILED DESCRIPTION

Overview

Figure 1A:
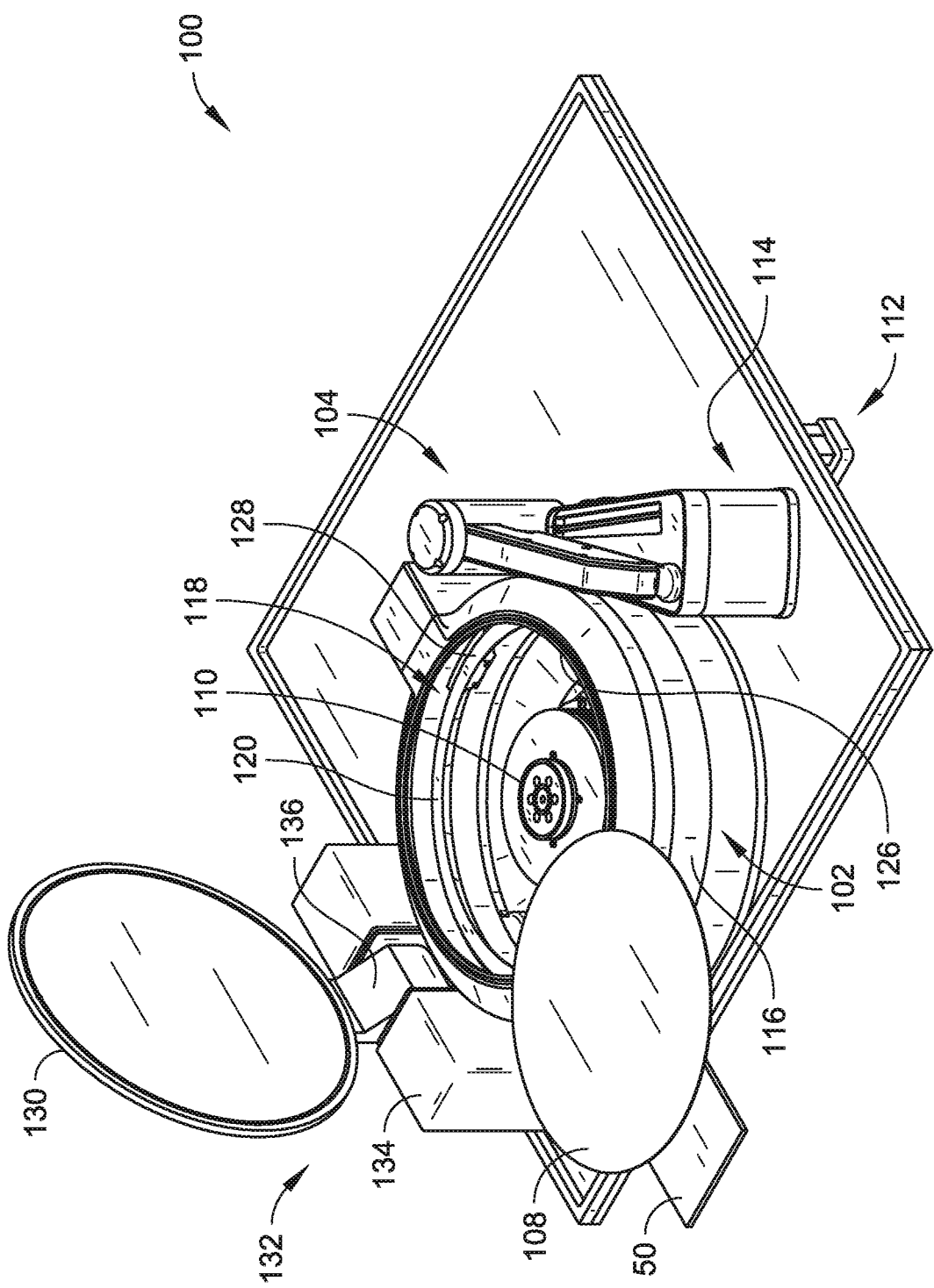
FIG. 1A is an isometric view of a system for integrated decomposition and scanning of a semiconducting wafer, in accordance with an embodiment of this disclosure.

Determination of trace elemental concentrations or amounts in a sample can provide an indication of purity of the sample, or an acceptability of the sample for use as a reagent, reactive component, or the like. For instance, in certain production or manufacturing processes (e.g., mining, metallurgy, semiconductor fabrication, pharmaceutical processing, etc.), the tolerances for impurities can be very strict, for example, on the order of fractions of parts per billion. For semiconductor wafer processing, the wafer is tested for impurities, such as metallic impurities, that can degrade the capabilities of the wafer or render the wafer inoperable due to diminished carrier lifetimes, dielectric breakdown of wafer components, and the like.

Vapor phase decomposition (VPD) and subsequent scanning of the wafer is a technique to analyze the composition of the wafer to determine whether metallic impurities are present. Traditional VPD and scanning techniques have limited throughput for facilitating the treatment and scanning of silicon wafers for impurity analysis. For instance, systems often utilize separate chambers for the VPD procedure and for the scanning procedure. In the VPD chamber, silicon dioxide and other metallic impurities present at the surface are contacted with a vapor (e.g., hydrofluoric acid (HF), hydrogen peroxide ($H_2O_2$), combinations thereof) and removed from the surface as vapor (e.g., as silicon tetrafluoride ($SiF_4$)). The treated wafer is transported to a separate chamber for scanning, where a liquid droplet is introduced to the treated wafer surface to collect residue following reaction of the decomposition vapor with the wafer. The scanning procedure can involve holding a droplet on the surface of the wafer with a scan head and rotating the wafer, while moving the scan head or keeping the scan head stationary to move the droplet over the surface. After multiple revolutions of the wafer, the droplet interacts with the desired surface area of the wafer to draw any residue from the contacted surface following decomposition. However, traditional wafer treatment techniques require significant amounts of time and equipment to process a wafer, such through movement of the wafer from a decomposition chamber to a scan chamber to a rinse chamber during treatment, utilizing scan nozzles that have limited droplet interaction with the wafer surface during scanning (i.e., requiring multiple revolutions of the wafer to interact the droplet with the entire surface area or a portion thereof), and the like. Moreover, such handling of the wafer can potentially expose technicians or other individuals to toxic hydrofluoric acid or can increase the risk of environmental contamination to the wafer during transfer of the wafer between the various process chambers, which also require a substantial physical process floor footprint to facilitate the equipment and transfer mechanisms between the equipment.

Accordingly, the present disclosure is directed, at least in part, to systems and methods for semiconductor wafer decomposition and scanning, where a chamber facilitates decomposition and scanning of the semiconducting wafer with a single chamber footprint, and where a nozzle directs a stream of fluid along a surface of the semiconducting wafer between a first port of the nozzle and a second port of the nozzle guided by a nozzle hood defining an elongated channel to direct the stream along the wafer surface. The chamber defines at least two apertures through which the semiconducting wafer can pass through operation of a wafer support and associated motor system, with a ledge to provide zones within the chamber for decomposition and rinsing while controlling fluid movement within the chamber, such as for draining and preventing cross contamination. The motor system controls a vertical position of the wafer support with respect to the chamber body to move the semiconductor within the chamber body, with positioning above the chamber body supported by the motor system to load and unload wafers, provide access to the nozzle, and the like. The chamber further incorporates a nebulizer to direct decomposition fluid that is aerosolized by the nebulizer directly onto the surface of the semiconducting wafer while the wafer support positions the semiconducting wafer within an interior region of the chamber. A chamber can incorporate a lid that can open and close with respect to the chamber to isolate the interior region of the chamber from the region exterior to the chamber, such as during the decomposition process. The nozzle can be positioned with respect to the chamber by a rotatable scan arm, where the nozzle can be positioned away from the chamber to facilitate lid closure (e.g., during the decomposition procedure) or to facilitate rinsing of the nozzle at a rinse station. Further, the rotation scan arm can position the nozzle over the semiconducting wafer during the scanning procedure. The system can utilize a fluid handling system including switchable selector valves and pumps to control introduction of fluid to the nozzle, from the surface of the wafer, for preparation of blanks, for rinsing system components, and the like. Following or during the scanning procedure, the scanning fluid can be collected and sent to an analysis device (e.g., ICPMS device) for analytical determination of the composition of the scanning fluid.

Example Implementations

FIGS. 1A through 10 illustrate aspects of a system for integrated decomposition and scanning of a semiconducting wafer ("system 100") in accordance with various embodiments of this disclosure. The system 100 generally includes a chamber 102, a scan arm assembly 104, and a fluid handling system 106 (e.g., shown at least in part in FIGS. 9A-10) to facilitate at least decomposition and scanning procedures of a semiconducting wafer 108 (sometimes referred to herein as the "wafer") through introduction of decomposition fluids to the wafer and through introduction to and removal of scanning fluids from a surface of the wafer 108. The chamber 102 provides an environment for each of wafer decomposition and wafer scanning with a single chamber footprint, and includes a wafer support 110 to hold the wafer 108 and a motor system 112 to control a vertical position of the wafer support 110 with respect to the chamber 102 (e.g., within the chamber 102, above the chamber 102, etc.) to position the wafer 108 for the decomposition and scanning procedures or during other procedures of the system 100. The motor system 112 additionally provides rotational control of the wafer support 110 to rotate the wafer 108 during various procedures of the system 100, and provides rotational and vertical control of the scan arm assembly 104 to bring a nozzle of the scan arm assembly 104 into positions over the wafer 108 during scanning procedures and into positions of a rinse station 114 for nozzle cleaning. In implementations, the wafer support 110 includes a vacuum table to hold the wafer 108 fixed relative to the wafer support 110, such as during movement of the wafer support 110.

The chamber 102 includes a chamber body 116 defining an interior region 118 to receive the wafer 108 for processing. A ledge 120 projects into the interior region 118 between a top portion 122 of the chamber body 116 and a bottom portion 124 of the chamber body 116. In implementations, the chamber body 116 defines a first aperture 126 at the top portion 122 through which the wafer 108 can be received into the interior region 118. In implementations, the ledge 120 defines a second aperture 128 at an intermediate portion of the interior region 118 between the top portion 122 and the bottom portion 124 (e.g., between the first aperture 126 and the bottom portion 124). During an example operation shown in FIG. 1A, the system 100 can receive a semiconducting wafer 108 onto the wafer support 110, such as through operation of an automated arm 50 selecting a wafer 108 from a front end unified pod (FOUP) or other location and introducing the selected wafer 108 onto the wafer support 110 (e.g., centered on the wafer support 110). The motor system 112 can position the wafer support 110 at, above, or adjacent to the top portion 122 of the chamber body 116 to permit access to the wafer support 110 by the automated arm 50 to set the wafer 108 onto the wafer support 110. For instance, the wafer support 110 can be positioned at a first position (e.g., shown in FIG. 2A) adjacent to the first aperture 126 during loading of the wafer 108. In implementations, the first position of the wafer support 110 is positioned outside the interior region 118 (e.g., extended through the first aperture 126) to receive the wafer 108.

The system 100 can include a lid 130 to isolate the interior region 118 from an exterior region 132 to facilitate wafer decomposition while limiting exposure of the decomposition fluid to the exterior region 132. For example, the lid 130 can have a size and a shape to cover the first aperture 126 when positioned over the first aperture 126. The lid 130 can be positionable between an open position (e.g., shown in FIG. 1A) and a closed position (e.g., shown in FIG. 1B). The open position can be utilized during wafer loading to provide access to the automated arm, during scanning procedures, during wafer unloading procedures, and the like. In implementations, the lid 130 is in the open position when the wafer support 110 is in the first position adjacent to the first aperture 126 to provide access to the wafer 108 by the nozzle of the scan arm assembly 104. The closed position can be utilized during wafer decomposition procedures to prevent the decomposition fluid from leaving the chamber 102 through the first aperture 126. In implementations, at least a portion of the lid 130 contacts the chamber body 116 to isolate the interior region 118 from the exterior region 132. The wafer 108 is moved within the interior region 118 through control of the vertical position of the wafer support 110 by the motor system 112 to a second position. For instance, the motor system 112 moves the wafer support 110 to the second position within the interior region 118 prior to or during movement of the lid 130 from the open position to the closed position. In implementations, the lid 130 is positioned adjacent the chamber body 116 and rotatably coupled to a mount 134 via a lid arm 136 to transition the lid 130 between the open position and the closed position.

Figure 1B:
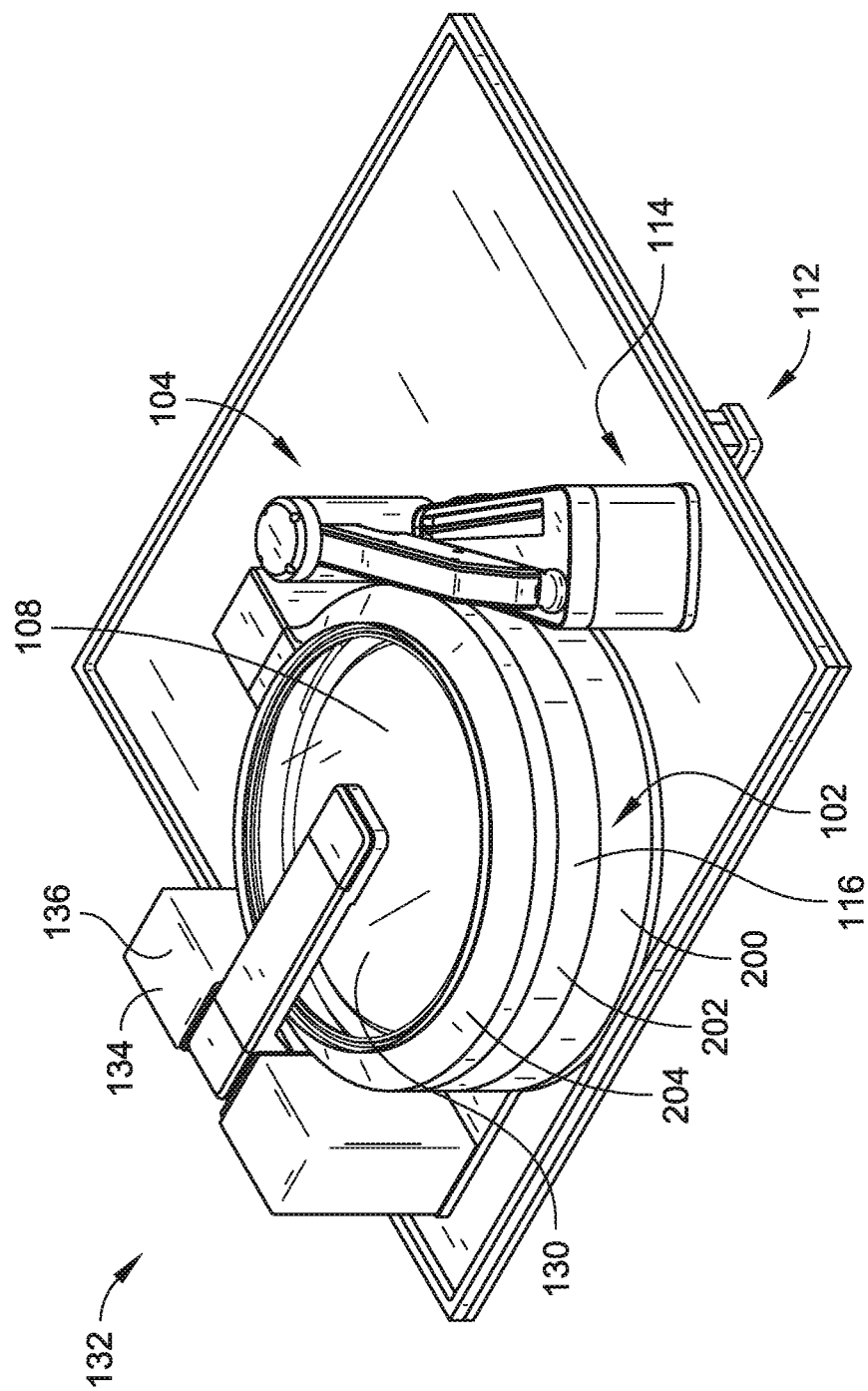
FIG. 1B is an isometric view of the system of FIG. 1A with a semiconducting wafer positioned within a chamber.
Figure 2A:
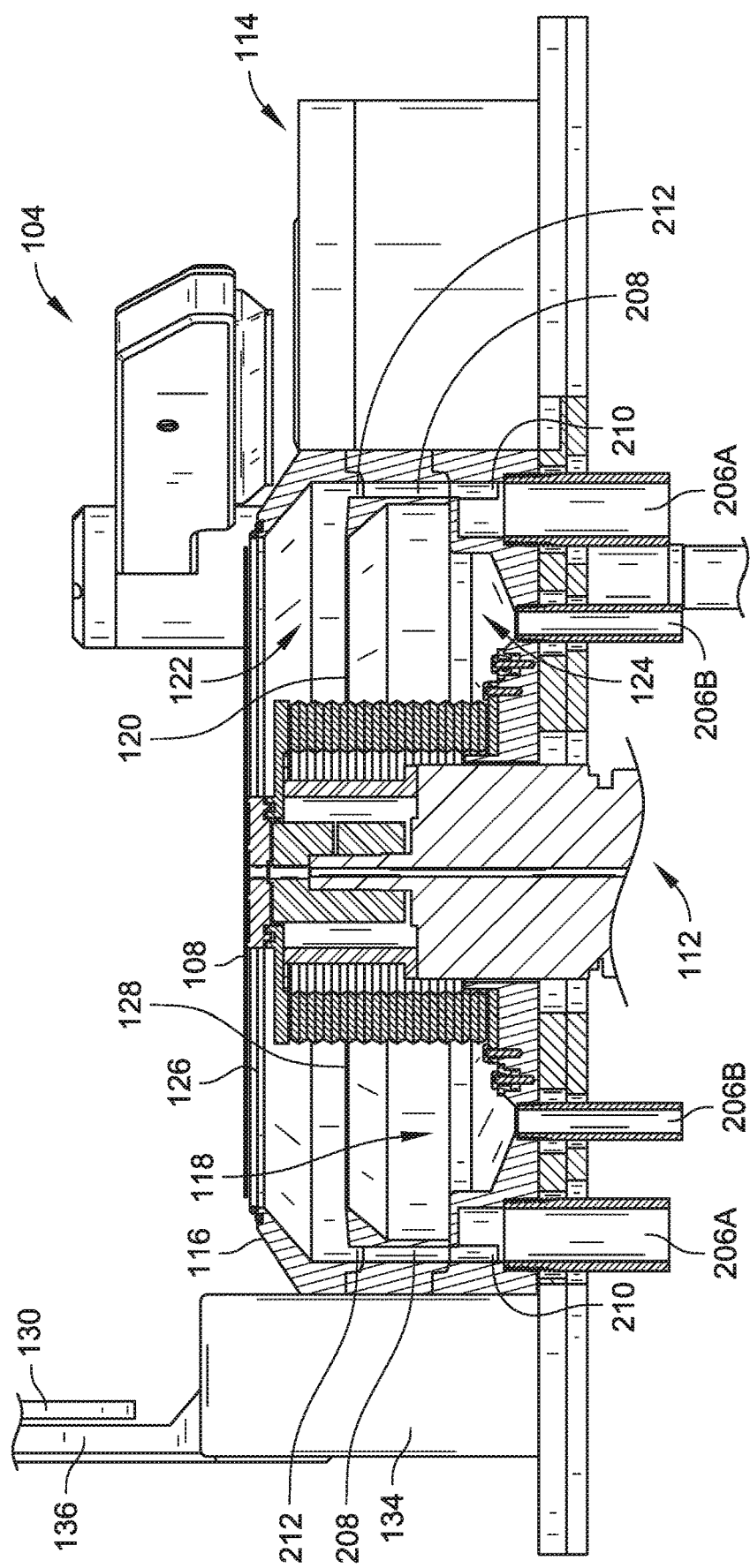
FIG. 2A is cross-sectional view of the system of FIG. 1A, with the semiconducting wafer positioned at a scanning position.
Figure 2B:
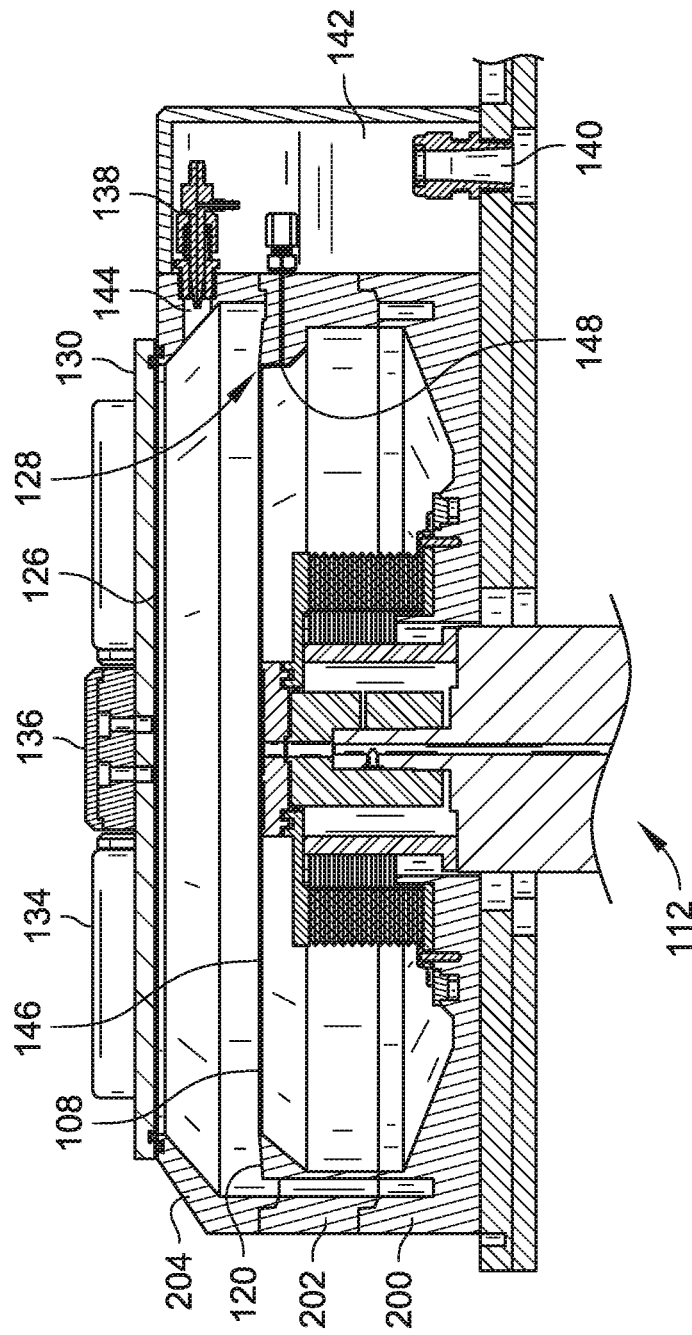
FIG. 2B is a cross-sectional view of the system of FIG. 1A, with the semiconducting wafer positioned at a decomposition position.

Following introduction of the wafer 108 to the wafer support 110, the system 100 can transition to a decomposition configuration to facilitate decomposition of one or more surfaces or edges of the wafer 108. For example, the motor system 112 moves the wafer support 110 from the first position to the second position to position the wafer 108 adjacent the second aperture 128 of the ledge 120 (e.g., as shown in FIGS. 1B and 2B). In implementations, the chamber 102 includes a nebulizer 138 positioned between the first aperture 126 and the second aperture 128 to spray a decomposition fluid onto the surface of the wafer 108 when the wafer support 110 is positioned at the second position by the motor system 112. The decomposition fluid is therefore sprayed directly into the chamber 102 by the nebulizer 138. The decomposition fluid can be supplied to the nebulizer 138 via one or more fluids lines from the fluid handling system 106, such as through a conduit 140 into an antechamber 142 housing at least a portion of the nebulizer 138. In implementations, at least a portion of the nebulizer 138 is disposed at least partially within a wall of the chamber 102. For example, the chamber body 116 can define an aperture 144 between the interior region 118 and the antechamber 142 where an outlet of the nebulizer 138 can dispense aerosolized decomposition fluid into the interior region between the first aperture 126 and the second aperture 128 to cover and decompose at least an upper surface 146 of the wafer 108.

In implementations, the chamber 102 induces a pressure beneath the wafer 108 during decomposition to prevent decomposition fluid from passing between the edge of the wafer 108 and the ledge 120. For example, the chamber 102 can include a gas outlet port 148 within the interior region 118 positioned between the second aperture 128 and the bottom portion 124 of the chamber body 116 to introduce a gas or other fluid into the interior region 118 during introduction of the decomposition fluid from the nebulizer 138 into the interior region 118. The gas from the gas outlet port 148 can be introduced at a pressure greater than the pressure of aerosolized decomposition fluid supplied from the nebulizer 138 to provide an upward flow of the gas through the second aperture 128 (e.g., between the edge of the wafer 108 and the ledge 120) to prevent the passage of the decomposition fluid beneath the wafer 108. In implementations, the system 100 includes a controller coupled to a gas source to introduce gas from the gas source to the gas outlet port 148 during introduction of the decomposition fluid onto the surface 146 of the wafer 108 by the nebulizer 138 when the wafer support 110 is positioned at the second position. For example, the gas can be fed to the gas outlet port 148 via a fluid line through the conduit 140 and the antechamber 142. In implementations, the motor system 112 induces rotation of the wafer support 110 during the decomposition procedure to spin the wafer 108 when the aerosolized decomposition fluid is present in the interior region 118.

The chamber 102 can facilitate removal of the fluids from the interior region 118 through one or more channels in the chamber body 116 in fluid communication with one or more drains, where such fluids can include, for example, excess decomposition fluid, silicon tetrafluoride ($SiF_4$), gas supplied by the gas outlet port 148, water, water vapor, rinse fluids, or other fluids. For example, the chamber body 116 can include a base portion 200, an intermediate portion 202, and a top portion 204 (e.g., shown in FIG. 2B) stacked on each other (e.g., via interlocking grooves). The base portion 200 can define one or more drains 206 (e.g., drains 206A and 206B) providing an outlet from the interior region 118 of the chamber 102 to one or more drain receptacles (not shown) via drain conduits. In implementations, drain 206A is fluidically coupled with channels in the chamber body 116 to provide access of fluids located between the first aperture 126 and the second aperture 128 to the drain 206A. For example, the intermediate portion 202 can define one or more channels 208 at least a portion of which extend through the intermediate portion to vertically align with at least a portion of one or more channels 210 formed by the base portion 200. The channels 208 can be positioned between an interior surface 212 of the chamber body 116 (e.g., of the top portion 204, the intermediate portion 202, or combinations thereof) and the ledge 120 to permit flow of fluids held in the interior region 118 between the lid 130 and the second aperture 128 or the surface 146 of the wafer 108 into the channels 208, through to the channels 210, and out the drains 206A. In implementations, the drains 206B permit rinse fluids or other fluids to leave the interior region 118 of the chamber 102 during rinse procedures (described herein with reference to FIG. 2C).

Following decomposition of the wafer 108, the system 100 can transition to a scanning configuration to permit access to the surface 146 of the wafer 108 by the scan arm assembly 104 without transferring the wafer 108 to a separate scanning system. To transition to the scanning configuration, the motor system 112 can position the wafer support 110 from the second position adjacent the second aperture 128 to the first position adjacent the first aperture 126, or otherwise closer to the top portion 122 of the chamber body 116 to permit access to the surface 146 of the wafer 108 by the scan arm assembly 104. The scan arm assembly 104 generally includes a rotatable arm support 300 coupled to a nozzle housing 302 that supports a nozzle 304 configured to introduce the scan fluid to the surface 146 of the wafer 108 and recover the scan fluid from the surface 146 of the wafer 108. The motor system 112 can control rotation of the rotatable arm support 300, vertical positioning of the rotatable arm support 300, or combinations thereof, to position nozzle housing 302 and nozzle 304 from one or more positions at the rinse station 114 (e.g., shown in FIG. 2A) to one or more positions adjacent or above the wafer 108 (e.g., shown in FIG. 4). An example implementation of the nozzle 304 is described further herein with reference to FIGS. 7A through 7D. In implementations, the rotatable arm support 300 rotates or otherwise moves the nozzle 304 to position the nozzle 304 adjacent the wafer 108 when the wafer support 110 is positioned at the first position by the motor system 112 and to position the nozzle 304 outside a path of the lid 130 from the open position to the closed position when the wafer support 110 is positioned at the second position by the motor system 112.

With the nozzle 304 in position adjacent or above the wafer 108 (e.g., shown in FIG. 4), the fluid handling system 106 can control introduction of scanning fluids to and from the nozzle 304 to facilitate scanning procedures of the surface 146 of the wafer 108. Referring to FIGS. 7A through 7D, an example implementation of the nozzle 304 is shown. The nozzle 304 is configured to deliver a stream of fluid across the surface 146 of the wafer 108, which can cover a greater surface area of the wafer 108 in a shorter period of time than moving a spot-size droplet over the wafer 108. The stream of fluid is guided over the surface 146 of the wafer 108 by the nozzle 304 to controllably scan the desired surface area of the wafer 108. In implementations, the nozzle 304 guides the stream of fluid over substantially the entire surface 146 in a single revolution of the wafer 108. In implementations, a wedge of the surface 146 (e.g., a sector of the wafer 108 or portion thereof) can be scanned in a fraction of a single revolution of the wafer 108. The nozzle 304 includes a nozzle body 500 defining an inlet port 502, an outlet port 504, a first nozzle port 506, a second nozzle port 508, and a nozzle hood 510. The nozzle 304 can also include one or more mounting apertures to mount the nozzle 304 within the nozzle housing 302. The inlet port 502 and the outlet port 504 receive fluid lines to direct the flow of fluid into and out from the nozzle 304 during operation of the system 100. For example, the nozzle 304 receives fluid through action of a first pump (e.g., syringe pump) pushing the fluid from a holding line or loop (e.g., a sample holding loop) into the nozzle 304, where it is directed into the inlet port 502 and through a channel 503 in the nozzle body 500 fluidically connecting the inlet port 502 and the first nozzle port 506. The fluid is then deposited onto the surface 146 of the wafer 108 through the first nozzle port 506. The fluid is directed along the surface 146 of the wafer 108 as a continuous fluid stream via a channel 512 defined between the nozzle hood 510 and the nozzle body 500, where the fluid is subsequently removed from the surface 146 of the wafer 108. For example, the fluid can be removed from the surface 146 via action of a second pump (e.g., syringe pump) pulling the fluid through the second nozzle port 508 at the end of the channel 512 distal from the first nozzle port 506 through fluid communication between the outlet port 504 and the second nozzle port 508 through the nozzle body 500. As such, the fluid is permitted to contact the wafer 108 during transit from the first nozzle port 506 to the second nozzle port 508. The channel 512 permits a volume of fluid to travel over the wafer, assisted by the nozzle hood 510. In implementations, the channel 512 has a volume of approximately 300 μL. However, the volume of the channel 512 is not limited to 300 μL and can include volumes less than 300 μL and volumes greater than 300 μL. For example, the volume of the channel 512 can depend on the size of the wafer 108 being processed by the system 100 to provide a desired amount of fluid (e.g., scanning fluid) to the surface 146. The length of the channel 512 can be selected based on the size of the wafer 108 to be processed by the system 100, where in implementations, the channel 512 has a length of approximately the radius of the wafer 108. In implementations, the length of the channel 512 can be from approximately 20 mm to approximately 500 mm. For example, the length of the channel 512 can be approximately 150 mm (e.g., to accommodate a 300 mm diameter wafer), approximately 100 mm (e.g., to accommodate a 200 mm diameter wafer), approximately 225 mm (e.g., to accommodate a 450 mm diameter wafer).

Figure 7A:
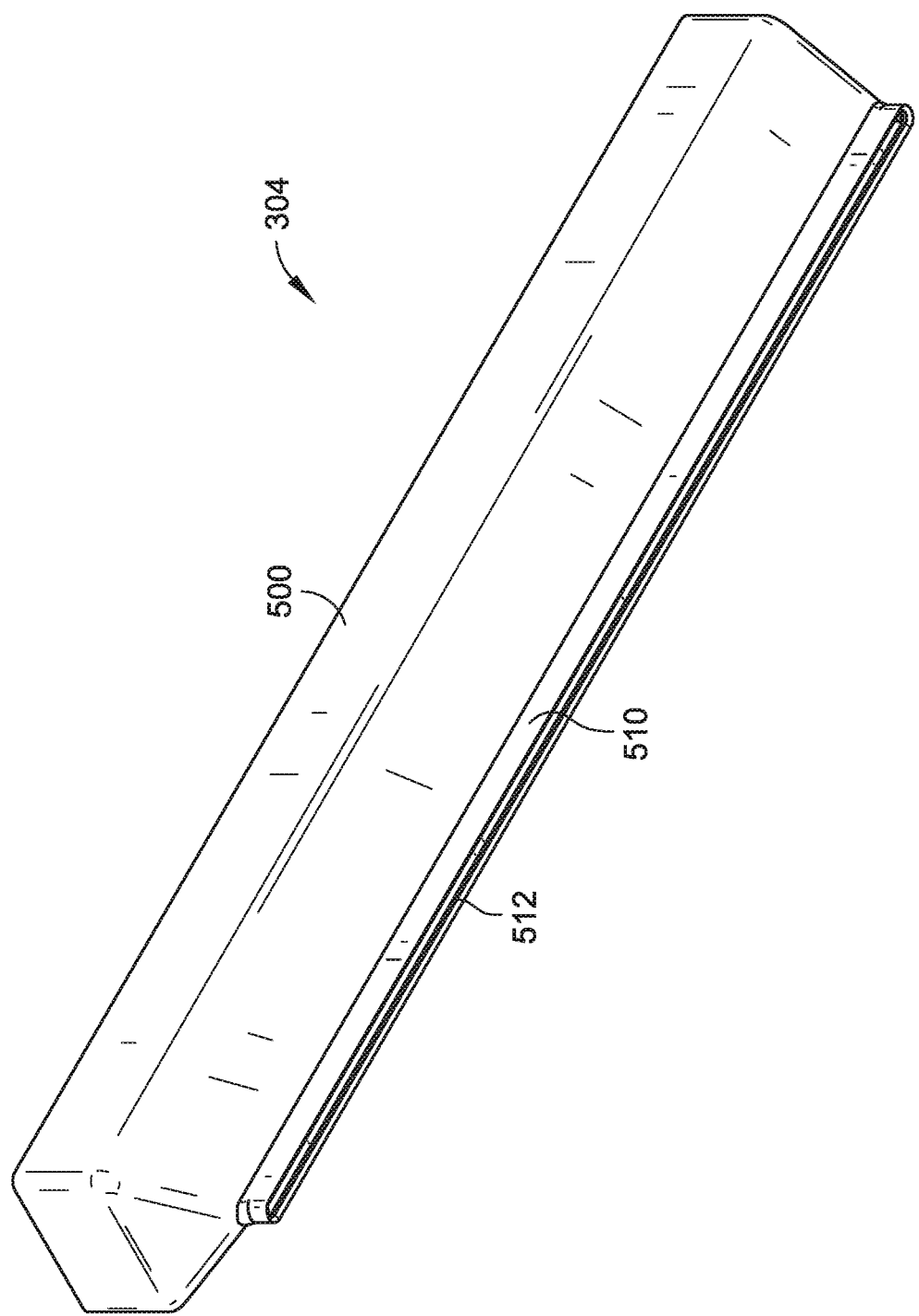
FIG. 7A is an isometric view of a nozzle for a semiconductor wafer decomposition and scanning system, in accordance with an embodiment of this disclosure.
Figure 7B:
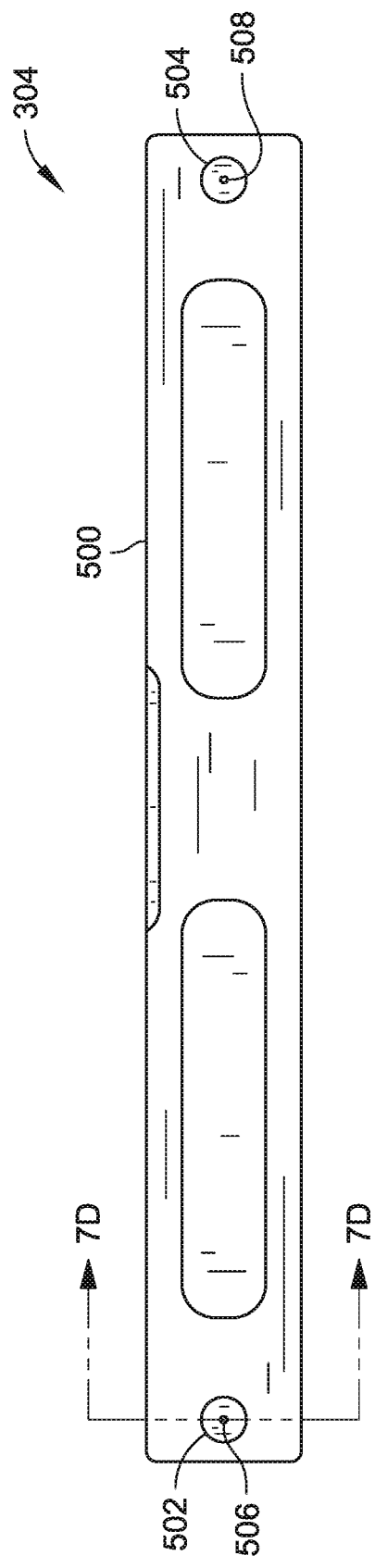
FIG. 7B is a top view of the nozzle of FIG. 7A.
Figure 7C:
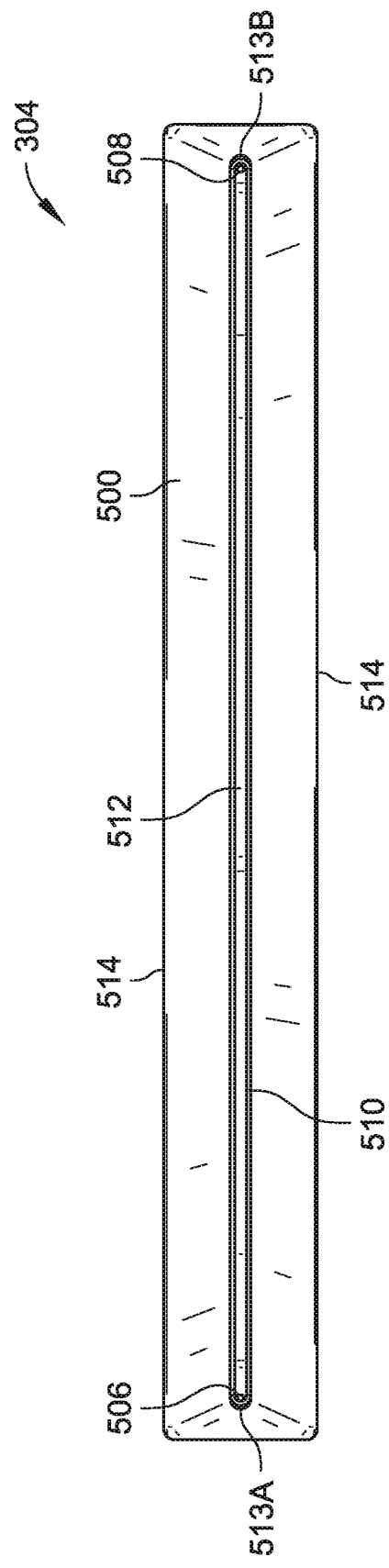
FIG. 7C is a bottom view of the nozzle of FIG. 7A.
Figure 7D:
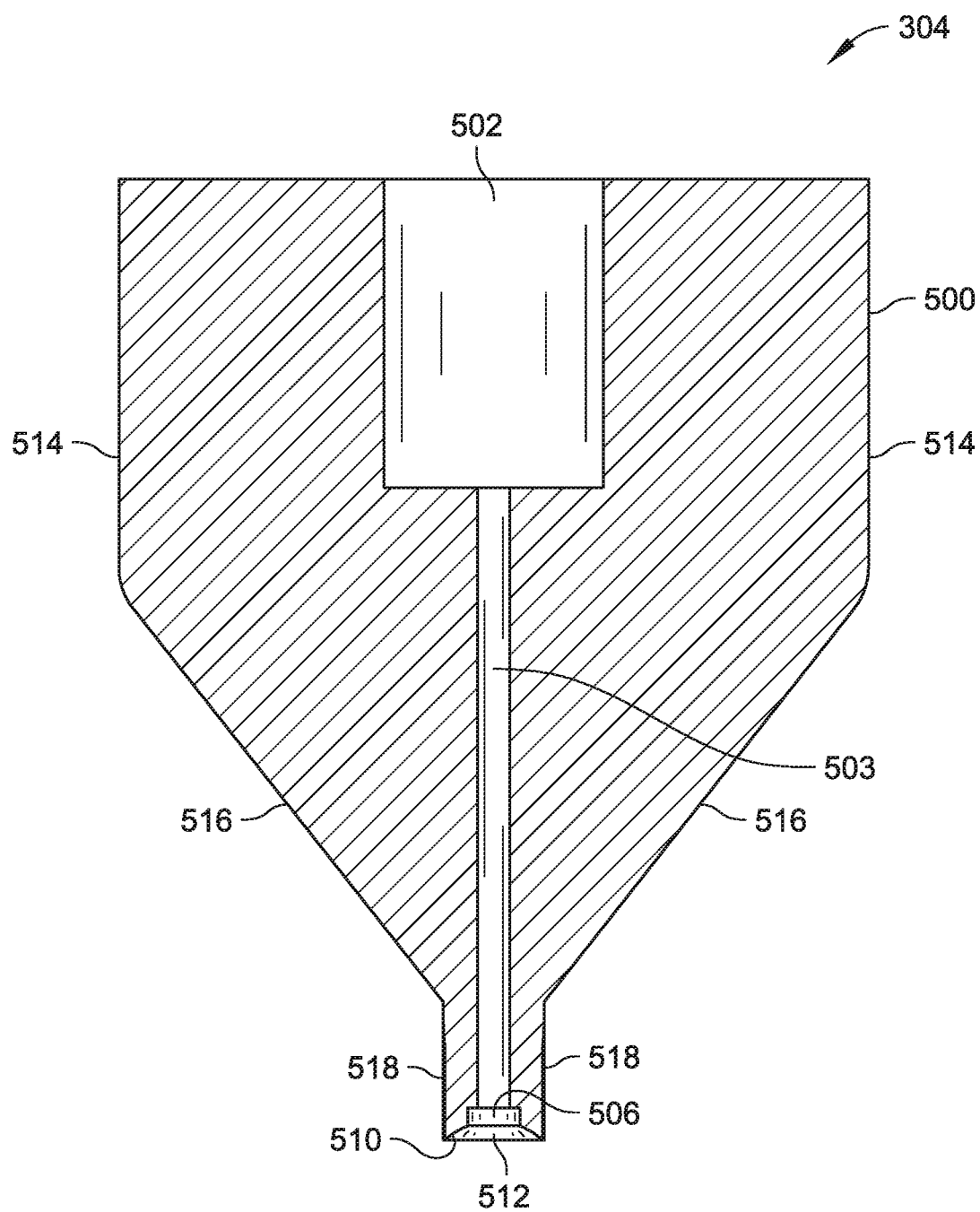
FIG. 7D is a cross-sectional view of the nozzle of FIG. 7B, taken along 7D-7D.

The nozzle hood 510 extends from the nozzle body 500 adjacent each of the first nozzle port 506 and the second nozzle port 508 and defines the channel 512 between the nozzle hood 510 and the nozzle body 500 between the first nozzle port 506 and the second nozzle port 508. The nozzle hood 510 can further extend to include each of the first nozzle port 506 and the second nozzle port 508 within the channel 512 such that the nozzle hood 510 encloses the first nozzle port 506 and the second nozzle port 508 within the nozzle hood 510 (e.g., as shown in FIG. 7C). In implementations, the nozzle body 500 includes substantially opposing side walls 514 longitudinally across the nozzle 304. The opposing side walls 514 each include a tapered wall portion 516 that are coupled to or otherwise extend to provide opposing portions 518. In implementations, the opposing portions 518 are substantially vertical to form at least a portion of the nozzle hood 510. The nozzle 304 can be formed from a single unitary piece, or portions of the nozzle 304 can be formed separately and fused or otherwise coupled together. In implementations, the nozzle 304 is formed from chlorotrifluoroethylene (CTFE), polytetrafluoroethylene (PTFE), or combinations thereof.

Figure 6:
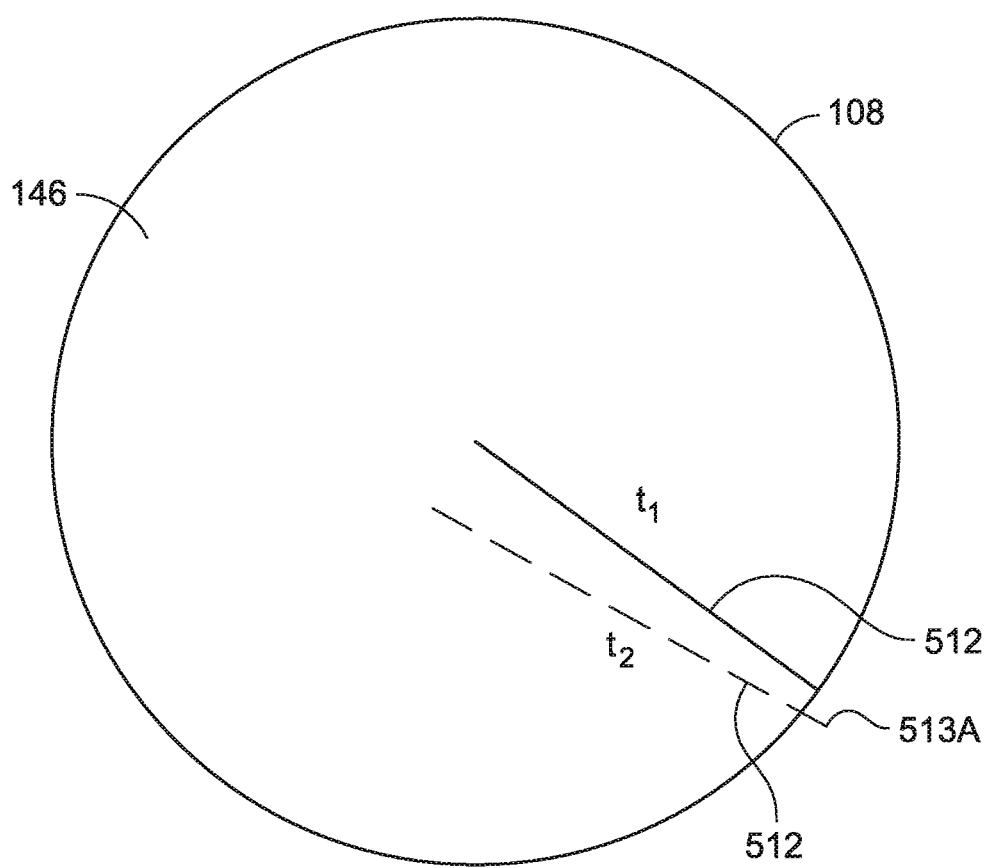
FIG. 6 is a top view of the scan arm positioned at a first position over the semiconducting wafer and a subsequent second position of the semiconducting wafer during a scanning process of the semiconducting wafer, in accordance with an embodiment of this disclosure.

The channel 512 of the nozzle 304 have an elongated shape with rounded ends 513A and 513B. Rounded ends can promote superior fluid handling characteristics as compared to angled ends, such as by providing more consistent delivery and uptake of fluid through the nozzle 304. In implementations, the first nozzle port 506 (where the fluid is dispensed from the nozzle 304 onto the wafer 108) is positioned tangent to the edge of the rounded end 513A of the channel 512. Such positioning can assist with a clean break of the fluid stream from the first nozzle port 506 once all fluid has been introduced to the wafer 108, while avoiding segmentation of the fluid on the surface of the wafer 108. In implementations, the rotatable arm support 300 rotates the nozzle housing 302 to cause the rounded end 513A of the nozzle 304 to extend over the edge of the wafer 108 (e.g., following the scan procedure) to promote uptake of the stream of fluid through the second nozzle port 508 via operation of the fluid handling system 106. For example, as shown in FIG. 6, the nozzle is positioned at a first position (e.g., a scan position) at a first time ($t_1$) whereby the channel 512 is positioned over the surface 146. The rotatable arm support 300 then rotates the nozzle housing 302 at a second time ($t_2$) to cause the rounded end 513A to extend past the edge of the wafer 108 (e.g., to overhang the edge) in a second position approximately 7 degrees rotated from the first position. In implementations, the second nozzle port 508 is positioned approximately at the center of the rounded end 513B distal from the first nozzle port 506. Positioning the second nozzle port 508 at the center of the rounded end 513B, as opposed to tangent to the edge of the rounded end 513B, can facilitate uptake of the fluid while facilitating the maintenance of the fluid stream on the surface 146 without segmentation of the fluid stream to precisely control movement of the fluid over the surface 146 of the wafer 108.

The position of the nozzle 304 above the surface 416 of the wafer 108 can influence the amount of fluid supported within the channel 512 during the scan procedure. The system 100 can include a zeroing procedure to ensure a desired height above the surface 416 is achieved prior to introduction of scanning fluid to the nozzle to facilitate the desired amount of fluid to be guided by the nozzle hood 510 along the surface 146 of the wafer 108. An example zeroing procedure is shown with respect to FIGS. 8A through 8C, where aspects of the scan arm assembly 104 are shown in accordance with various embodiments of this disclosure. The scan arm assembly 104 facilitates alignment of the nozzle 304 with respect to the wafer 108, such that the first nozzle port 506 and the second nozzle port 508 are level with respect to the surface 146 of the wafer 108 to which the fluid will be applied and removed. The system 100 can undergo an alignment or leveling procedure for each wafer 108 processed by the system 100 (e.g., in between scanning of a first wafer that is removed from the chamber 102 and scanning of a second wafer that is introduced to the chamber 102) or as needed to ensure the nozzle 304 is level with respect to the wafer 108 held by the chamber 102, such as prior to the next scanning procedure. In general, the nozzle 304 is movably coupled with a nozzle housing 302 to permit the nozzle 304 to have a range of motion with respect to the nozzle housing 302 while being supported by the nozzle housing 302. The nozzle housing 302 defines an aperture 520 through which at least a portion of the nozzle 304 can pass when transitioning between an extended position (e.g., shown in FIG. 8A) and a retracted position (e.g., shown in FIGS. 8B and 8C). For example, a top portion of the nozzle 304 can be positioned within the nozzle housing 302, where additional portions of the nozzle 304 can be introduced into the interior of the nozzle housing 302 via the aperture 520 when the nozzle 304 is transitioned from the extended portion to the retracted portion. For instance, when the nozzle 304 is positioned to contact a zeroing surface 522, the nozzle hood 128 can contact the surface 522 to push the nozzle 304 into a level position with respect to the surface 522. The nozzle housing 302 can then actuate to lock the position of the nozzle 304 in place, to keep the nozzle 304 level with the surface 522 when the nozzle 304 is lifted from the surface 522 (e.g., to a scan position). The nozzle housing 302 can include a mechanical, electrical, or electromechanical locking device to releasably secure the nozzle 304 with respect to the nozzle housing 302. In implementations, the surface 522 includes the surface 146 of the wafer 108, a surface of the wafer support 110 (e.g., prior to loading the wafer 108 onto the wafer support 110), a surface of rinse station 114, or another surface having a structure consistent with level characteristics of a semiconducting wafer, such that when the nozzle 304 contacts the surface 522, the nozzle hood 128, the first nozzle port 506, the second nozzle port 508, etc. will be properly positioned with respect to the wafer 108.

Figure 8B:
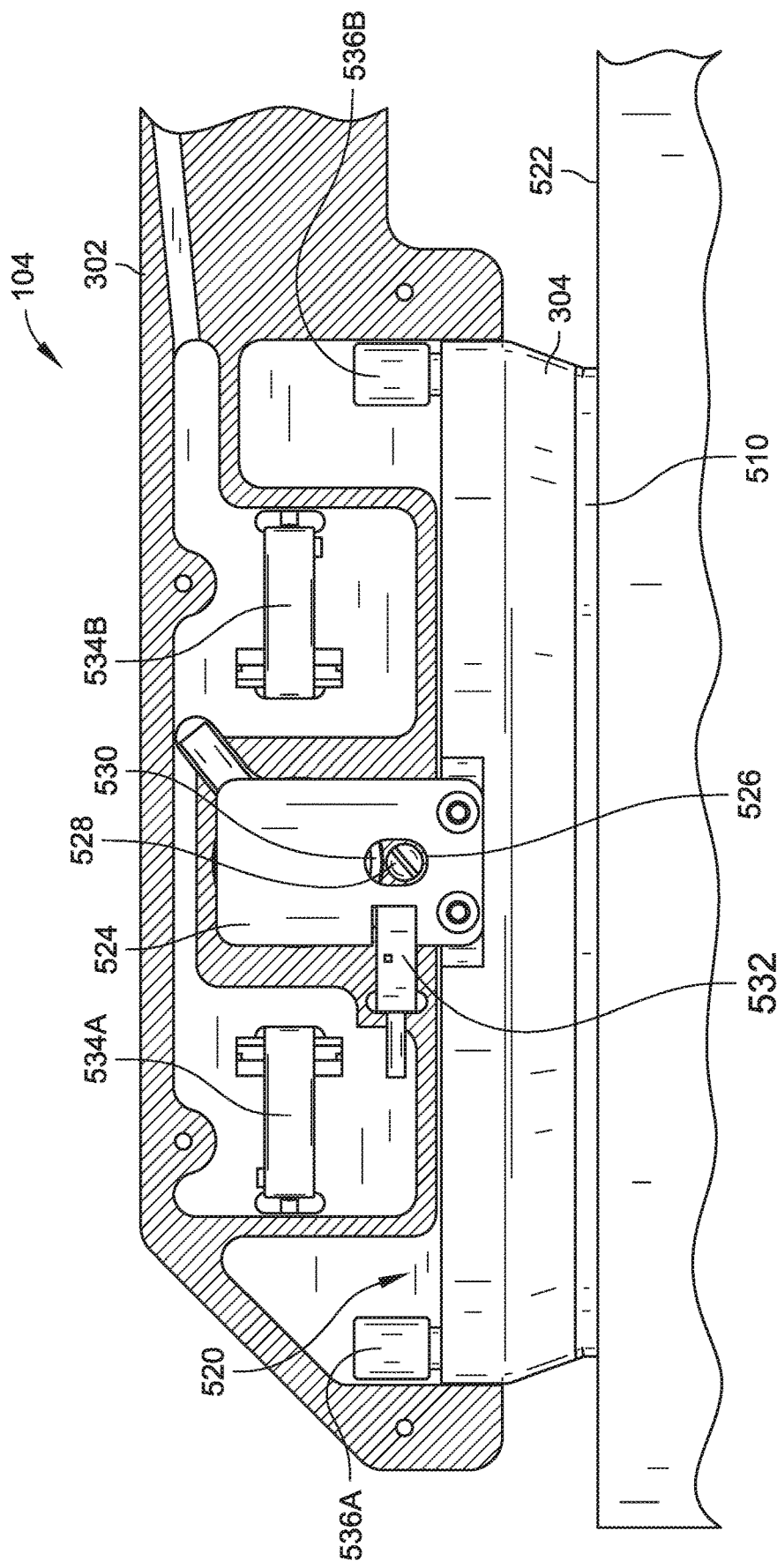
FIG. 8B is a partial cross-sectional view of the nozzle mount assembly of FIG. 8A in contact with a surface.

In implementations, the nozzle mount assembly 500 includes the nozzle housing 302 to couple the nozzle 304 to the rotatable arm support 300. The nozzle 304 can be coupled to the nozzle housing 302 via a coupler 524 defining an aperture 526 to interact with a protrusion 528 of the nozzle housing 302. The protrusion 528 can include a fastener, pin, or other structure having a width or diameter that is less than a width or diameter of the aperture 526, such that when the scan arm assembly 104 is in a first state (e.g., a leveling state), the top of the aperture 526 rests on the protrusion 528, which provides a lower or extended position of the nozzle 304 with respect to the nozzle housing 302 via the coupler 524 (e.g., as shown in FIG. 8A). The system 100 can implement an alignment or leveling procedure by causing the rotatable arm support 300 to lower the nozzle housing 302 to cause the nozzle 304 to contact the surface 522 (e.g., as shown in FIG. 8B). For example, as the nozzle 304 contacts the surface 522, the coupler 524 is pushed upwards with respect to the protrusion 528, such that the protrusion 528 does not support the coupler 524 via contact with the top of the aperture 526. Following contact of the nozzle 304 with the surface 522, the nozzle 304 is in the retracted position and the system 100 can actuate a lock structure 530 (e.g., integrated within the nozzle housing 302) to secure the position of the nozzle 304 with respect to the nozzle housing 302. For example, the coupler 524 can include a ferrous material to be secured by a magnetic field generated by an electromagnet incorporated in the lock structure 530. While an electromagnet is shown as part of the lock structure 530 in the example embodiments, other lock structures can be utilized, including but not limited to, pneumatic solenoid actuators, mechanical locks, electromechanical locks, or the like.

The nozzle housing 302 can include sensors to monitor a position of the nozzle 304 with respect to the nozzle housing 302, such as to determine whether the nozzle 304 is in the extended state, in the retracted state, or in a different position. For example, in implementations, the nozzle housing 302 includes a sensor 532 to detect the presence or absence of the coupler 524 and generate or cease generating a signal received by a controller of the system 100. The sensor 532 can include an optical switch with a light source on a first side of the coupler 524 and a detector on a second opposing side of the coupler 524. The coupler 524 can include an indexing cutout, a portion of which passes between the light source and the detector of the sensor 532. When the nozzle 304 is in the extended position (e.g., the lock structure 530 is not engaged), light from the light source passes through the indexing cutout of the coupler 524 and is detected by the detector on the other side of the coupler 524. The sensor 532 then outputs a signal or ceases outputting a signal indicating detection of the light, which indicates to the system 100 that the nozzle 304 is in the extended position. When the nozzle 304 is in the retracted position, such as after being leveled on the surface 522, the body of the coupler 524 is positioned between the light source and detector of the sensor 532, blocking the light from reaching the detector. The sensor 532 would output a signal or cease outputting a signal indicating no detection of the light source. Such a signal or lack thereof indicates to the system 100 that the nozzle 304 is in the retracted position (e.g., supported in the nozzle housing 302 by the lock structure 530). Operation of the sensor 532 can provide a system check to ensure that the nozzle 304 is still in a retracted and leveled position after a period of operation. Changes in the output from the sensor 532 can indicate that a releveling procedure may be appropriate, the lock structure 530 should be evaluated, etc. Alternatively, the indexing cutout could be repositioned such that when the nozzle 304 is in the retracted position, the detector is aligned with the indexing cutout, and when the nozzle 304 is in the extended position, the body of the coupler 524 blocks the light.

When the nozzle 304 is leveled with respect to the surface 522 and locked into position via the lock structure 530, the rotatable arm support 300 can lift the nozzle 304 from the surface 522 (e.g., as shown in FIG. 8C), while maintaining the nozzle 304 in the leveled position. The rotatable arm support 300 can then position the nozzle 304 in a scan position or otherwise move the nozzle 304 (e.g., to permit a wafer 108 to be positioned on the wafer support 110 if the surface 522 used to level the nozzle 304 is the support 106).

The nozzle housing 302 can include one or more sensors to facilitate introducing fluid to the nozzle 304 and removing fluid from the nozzle 304. For example, in implementations, the nozzle housing 302 includes one or more sensors (sensors 534A and 534B are shown) adjacent to or more of the inlet port 502 and the outlet port 504 of the nozzle 304 to control operation of the fluid handling system 106 to control the flow of fluid into and out of the nozzle 304. The sensors 534A and 534B can include an optical sensor, a capacitive sensor, an ultrasonic sensor, or other sensor, or combinations thereof to sense the flow of liquid or the absence thereof within the fluid lines of the system 100. For example, the system 100 can include fluid lines from the fluid handling system coupled to fluid line couplers 536A and 536B through which the sensors 534A and 534B, respectively, can detect the present or absence of fluid therein. Output signals, or the lack thereof, can control operation of one or more components of the fluid handling system 106 including, but not limited to, pumps utilized to introduce fluid to or remove fluid from the nozzle 304.

Figure 2C:
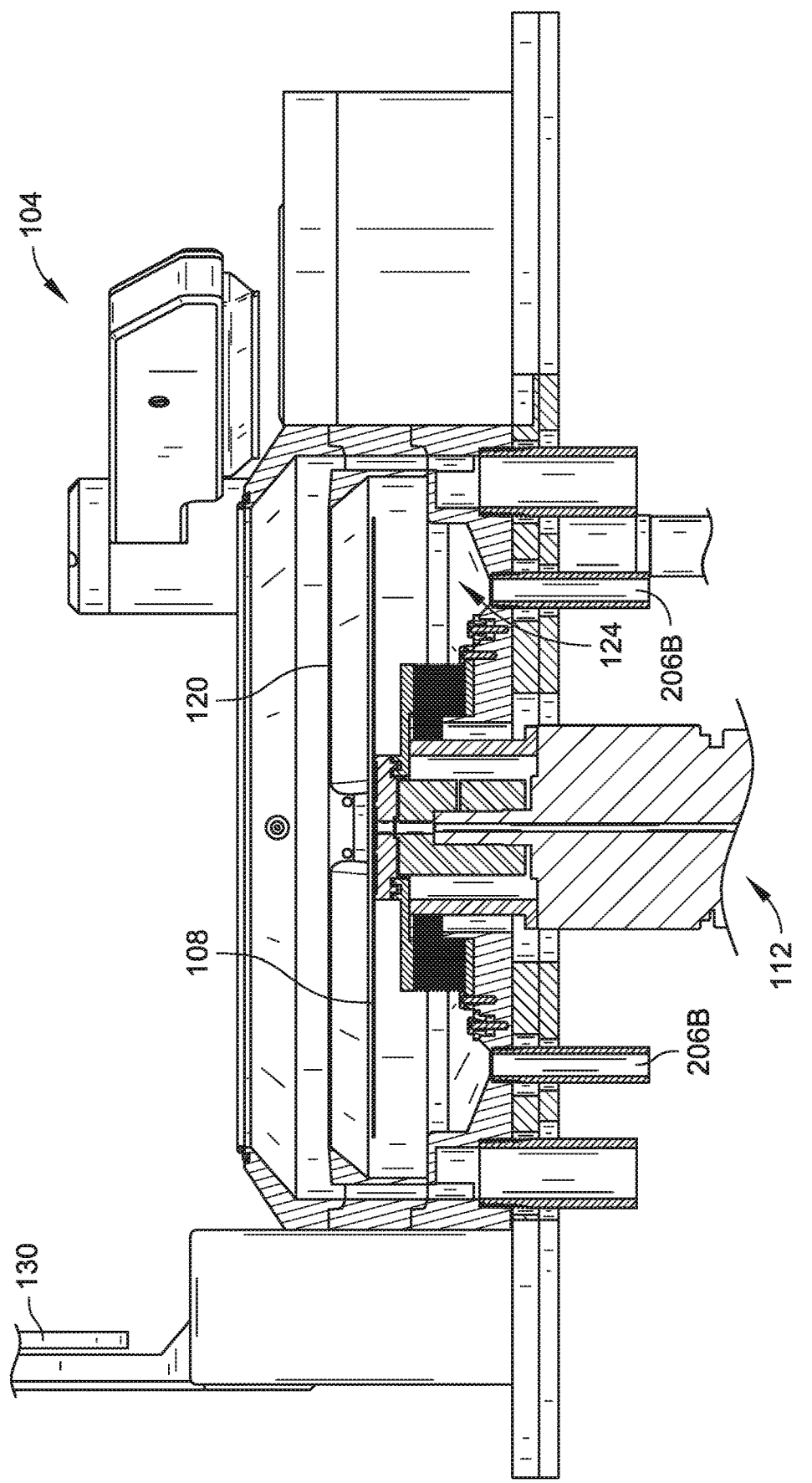
FIG. 2C is a cross-sectional view of the system of FIG. 1A, with the semiconducting wafer positioned at a rinse position.
Figure 3:
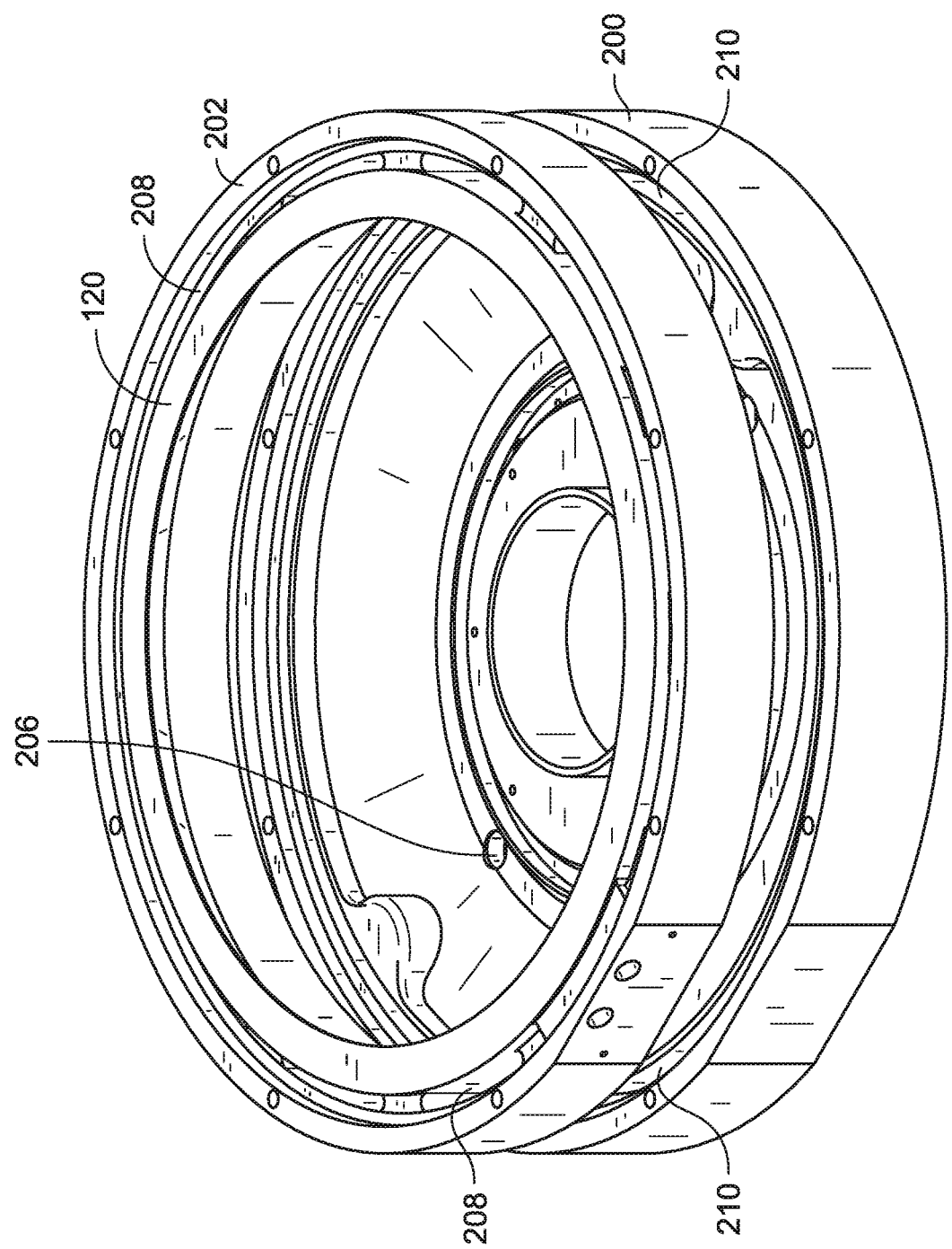
FIG. 3 is an isometric view of a portion of a chamber body of the system of FIG. 1A, in accordance with an embodiment of this disclosure.
Figure 4:
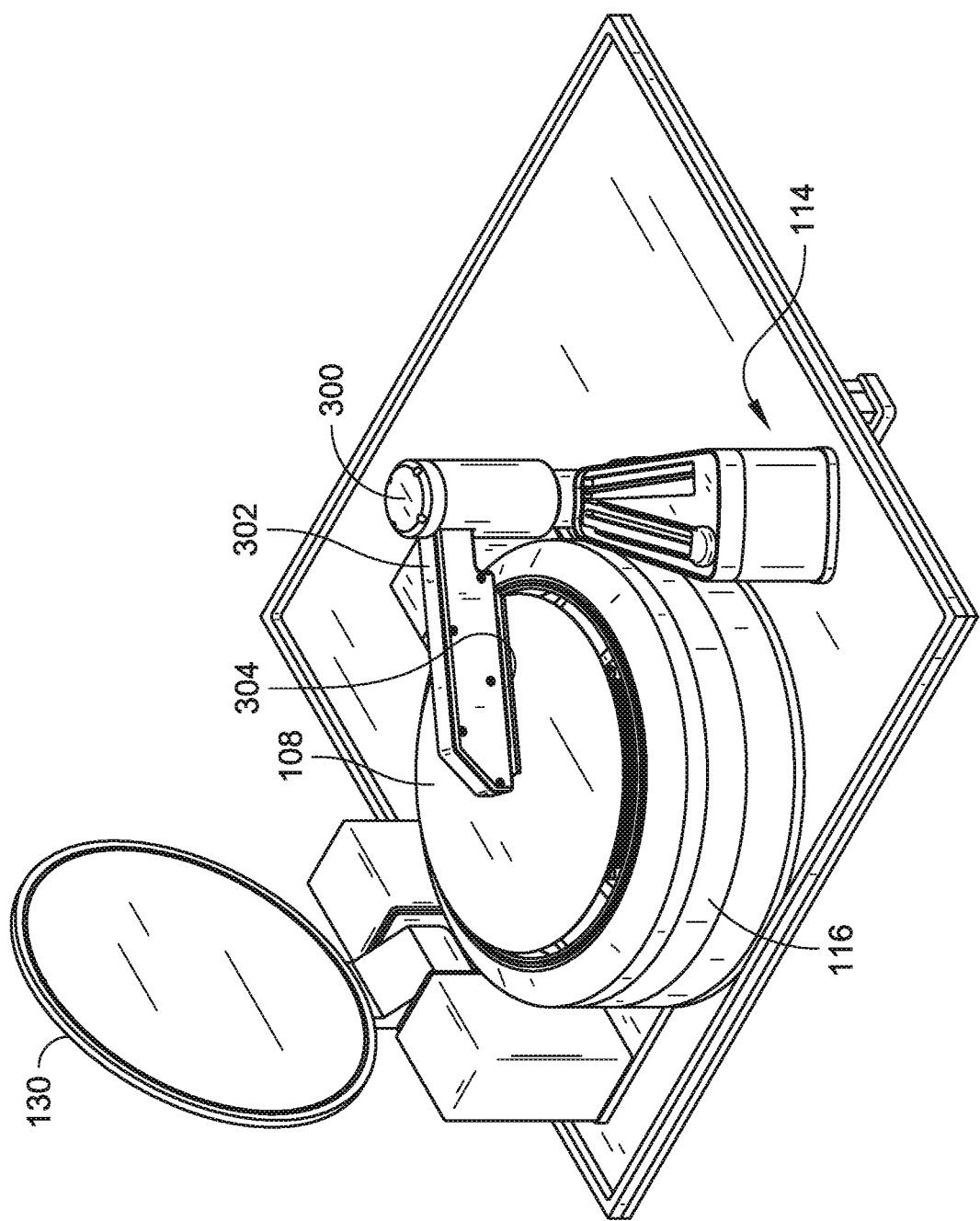
FIG. 4 is an isometric view of the system of FIG. 1A, with a scan arm positioning a nozzle over a surface of the semiconducting wafer positioned at a scanning position.
Figure 5:
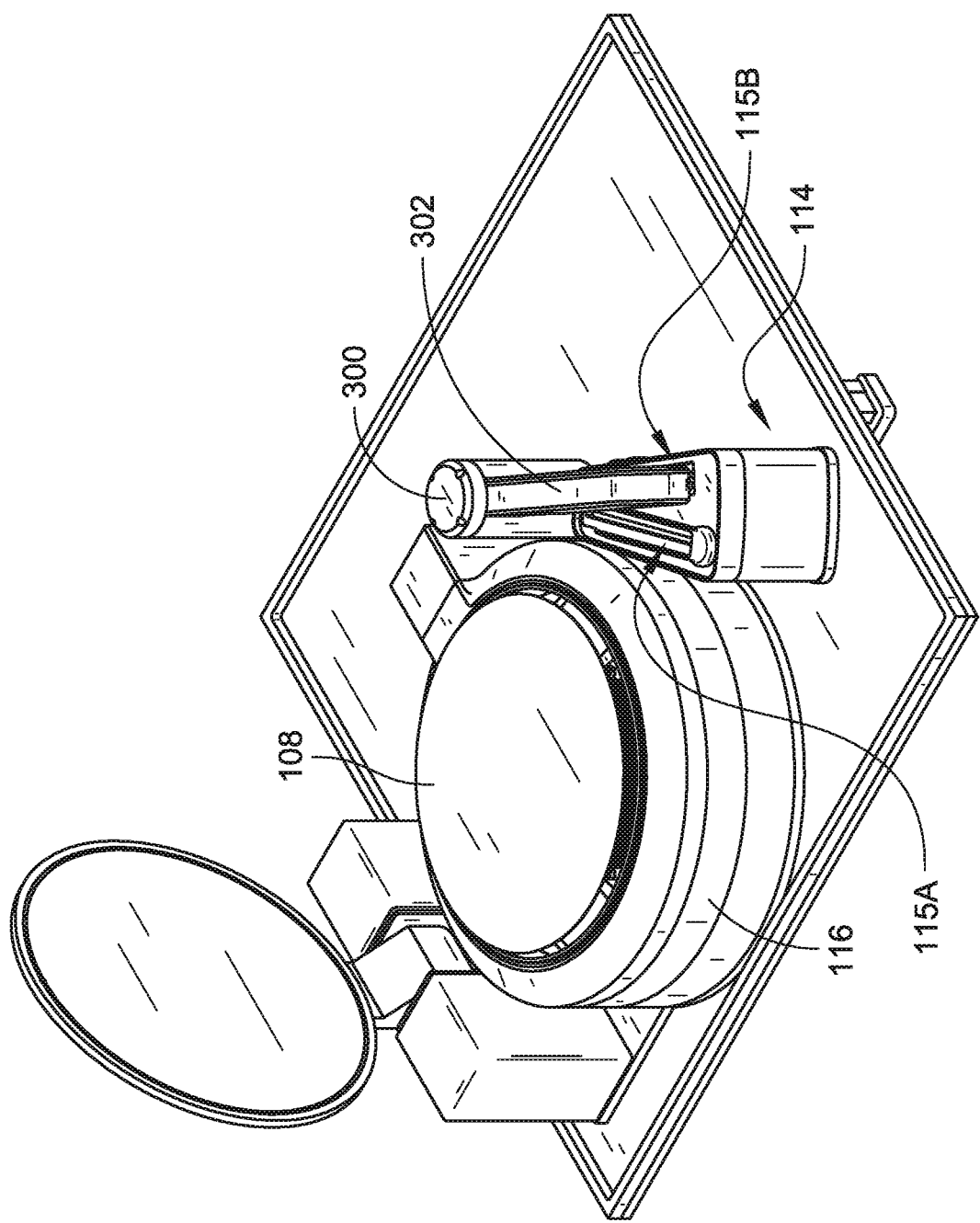
FIG. 5 is a partial isometric view of the system of FIG. 1A, with the scan arm positioned at a rinse station for the nozzle.

The system 100 facilitates rinsing procedures for the wafer 108 and for the nozzle 304, such as following scan procedures. Referring to FIG. 2C, the chamber 102 is shown in a rinse configuration to facilitate rinsing of the wafer 108. To transition to the rinse configuration, the motor system 112 can position the wafer support 110 from the first position adjacent the first aperture 126 (e.g., the scanning position) or other position to a rinse position between the ledge 120 and the bottom portion 124 of the chamber body 116. A rinse fluid can be introduced to the wafer 108, such as through a rinse port on the nozzle housing 302 or otherwise provided in the system 100, whereby the motor system 112 can spin the wafer 108 to induce removal of the rinse fluid. The rinse fluid can then impact the interior of the chamber body 116 and flow to the drains 206B to leave the interior region 118 of the chamber 102. To clean the nozzle 304, the rotatable arm support 300 can position the nozzle 304 with respect to one or more troughs of the rinse station 114. For instance, the rinse station 114 can include a first trough 115A (e.g., shown in FIG. 5) having an elongated channel into which rinse fluid is introduced from a rinse fluid source to interact with the nozzle hood 510, the channel 512, or other portions of the nozzle 304. The nozzle 304 is shown positioned in the first trough 115A in FIGS. 1A and 1B. The rinse station 114 can also include a second trough 115B having an elongated channel coupled with a drying gas source (e.g., nitrogen or other inert gas) to introduce a drying gas into the elongated channel to impact against the nozzle 304. The nozzle 304 is shown positioned in the second trough 115B in FIG. 5.

Figure 9A:
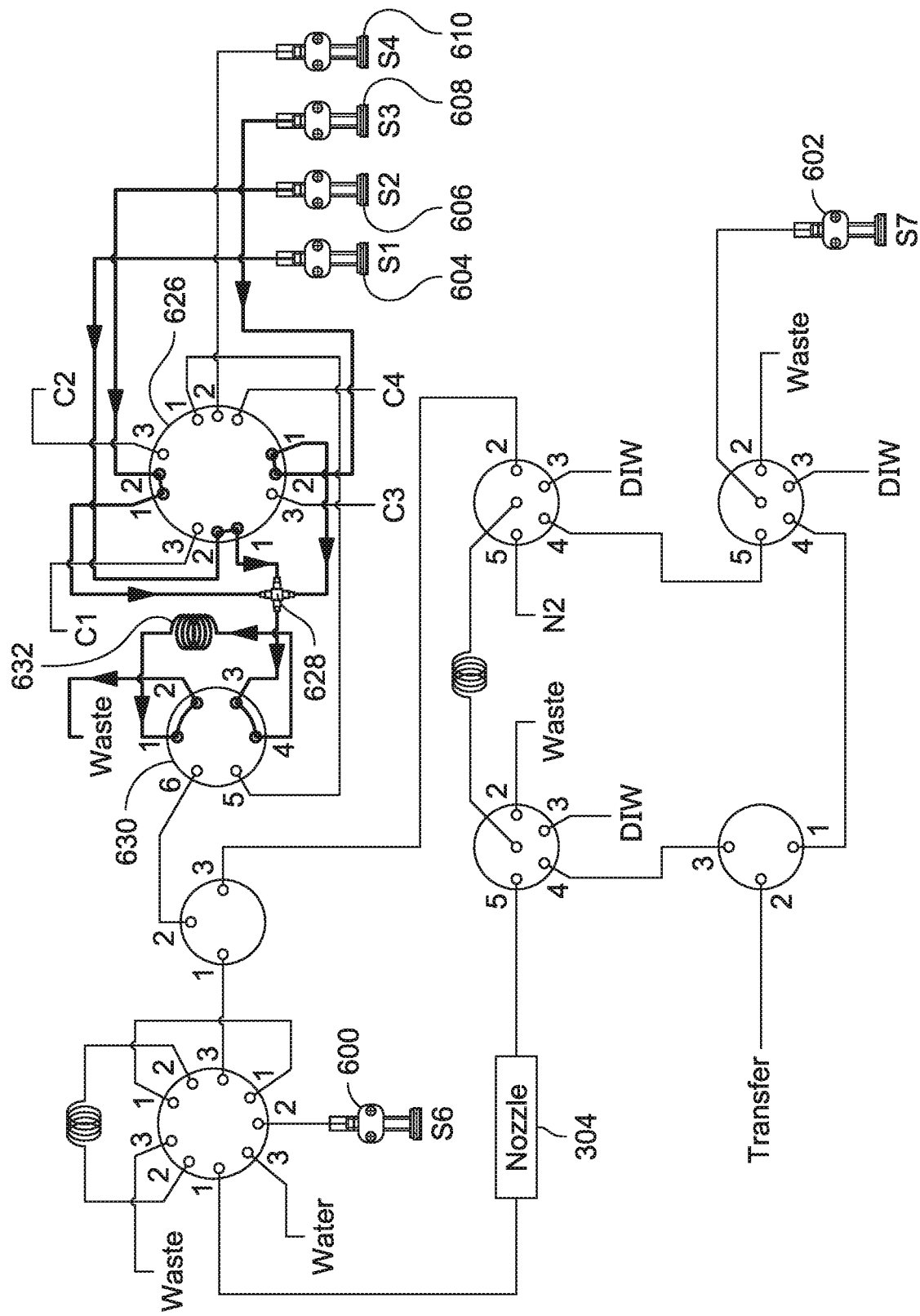
FIG. 9A is a schematic of a fluid handling system for a semiconductor wafer decomposition and scanning system, in accordance with an embodiment of this disclosure.

Referring now to FIGS. 9A through 10, an example fluid handling system 106 of system 100 is described in accordance with various embodiments of this disclosure. For example, the fluid handling system 106 can facilitate preparation of chemical blanks of chemicals utilized by the system 100 for analysis by an analytic system, can facilitate preparation of decomposition fluids on demand and according to desired ratios for use in the chamber 102, can facilitate preparation of scanning fluids on demand and according to desired ratios for use in the chamber 102, and combinations thereof. As shown, the fluid handling system 106 includes a pump system including pumps 600, 602, 604, 606, 608, 610, and 612 to draw and push fluids through the fluid handling system to interact with other components of the system 100 (e.g., the nozzle 304), analysis systems, and the like. The pump system is shown incorporating syringe pumps, however the system 100 can utilize different pumps types or systems, combinations of pump types or systems, and the like. An example configuration of the fluid handling system 106 is shown in FIG. 10 to introduce a decomposition fluid to the nebulizer 138 of the chamber 102 during the decomposition procedure of the wafer 108. The pump 612 can draw hydrofluoric acid (HF) or other decomposition fluid(s) from a decomposition fluid source 613 into a holding line (e.g., decomposition fluid holding loop 614) with a valve 616 in a first configuration and a valve 618 in a first configuration. In a second configuration of the valve 616 gas from a gas source 619 can be introduced into the fluid line holding the decomposition fluid to provide a barrier between a working fluid used to push the decomposition fluid to the nebulizer 138. In a second configuration of the valve 618, the pump 612 can draw a working solution (e.g., deionized water or other fluid), whereby the valve 618 can switch to the first position and the valve 616 can switch to a third configuration to provide fluid communication between the pump 612 and the nebulizer 138, whereby the pump 612 pushes the working solution against the decomposition fluid held in the decomposition fluid holding loop 614 (e.g., via any intermediate air gap) to introduce the decomposition fluid to the nebulizer 138. Following decomposition of the wafer 108, the system 100 can scan the wafer 108 for determination of impurities.

Referring to FIG. 9A, the fluid handling system 106 is shown in an example chemical load configuration. The pumps 604, 606, and 608 draw chemicals from chemical sources 620, 622, and 624, respectively, via valve 626 in a first valve configuration. The chemicals can include, for example, hydrofluoric acid (HF), hydrogen peroxide ($H_2O_2$), deionized water (DIW), or other fluids. In a second valve configuration (shown in FIG. 9A) of valve 626, each of pumps 604, 606, and 608 are fluidically coupled with a fluid line connector (e.g., manifold 628 or other connector) whereby the chemicals drawn by each pump are combined and permitted to mix. The combined fluids are directed to valve 630, which in a first valve configuration directs the combined fluids to a holding line (e.g., holding loop 632). In implementations, a system controller controls operation of each of pumps 604, 606, and 608 independently to control the flow rate of each fluid handled by the respective pumps, thereby providing a controlled composition of the mixed fluids directed into the holding loop 632 following mixing. In implementations, a first fluid mixture can be used to interact with the wafer 108 during a first scan procedure, and a second fluid mixture can be prepared on demand with different operational control of the pump systems 604, 606, and 608 to introduce the second fluid mixture to interact with the wafer 108 during a second scan procedure. Additional fluid mixtures can be prepared on demand and introduced to the wafer 108 as desired. In implementations, the holding loop 632 has a volume that supports scanning procedures for multiple wafers without need to refill. For example, the scanning solution can be prepared, where a portion of the scanning solution (e.g., a "blank" sample) can be sent to an analytic system for verification that the solution is within operational constraints for use on wafers. The remainder of the scanning solution in the holding loop 632 can then be used in multiple scanning procedures, with the scanning solution pre-verified as suitable for use. An example loading of a chemical blank for analysis is shown with reference to FIG. 9B.

Figure 9B:
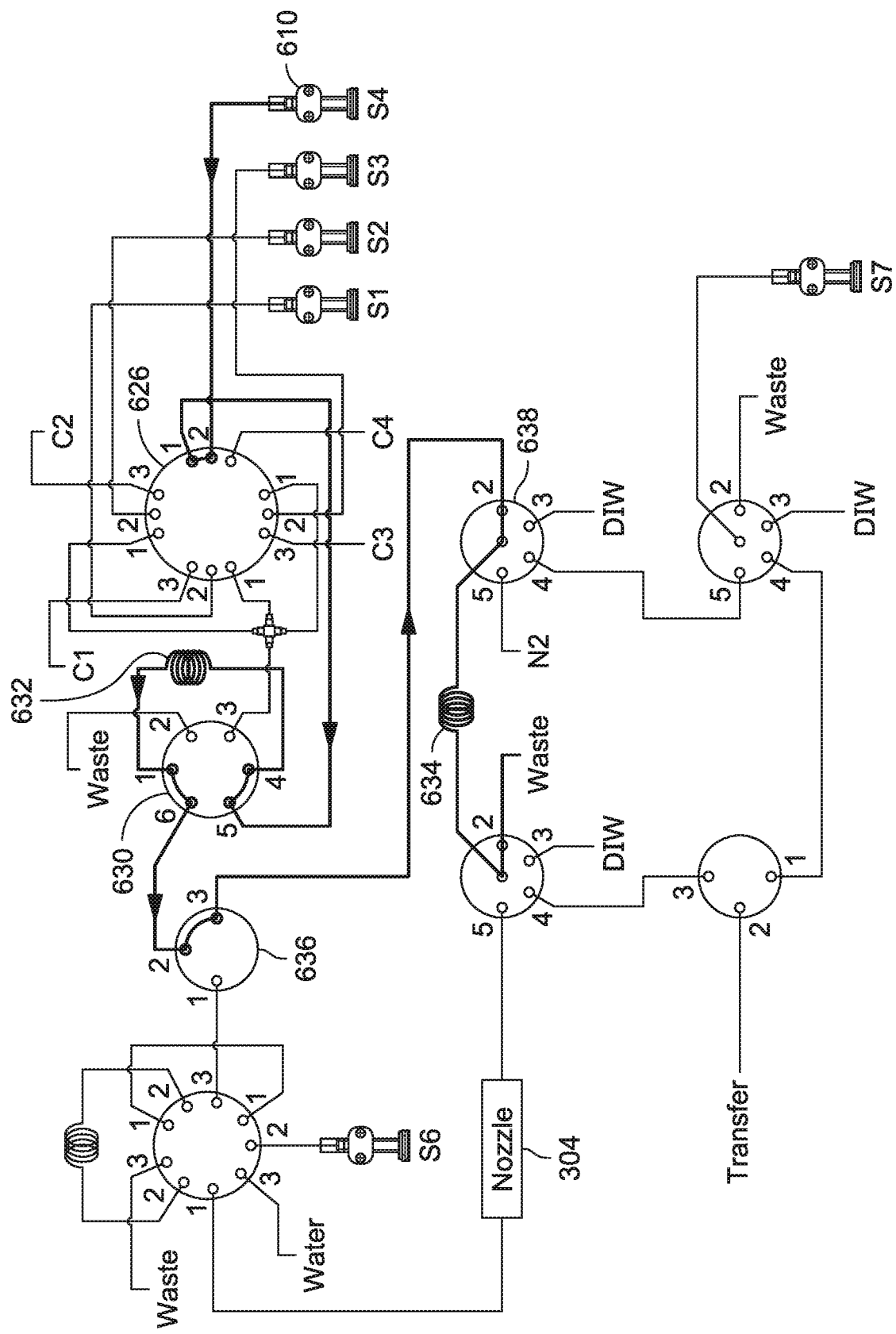
FIG. 9B is a schematic of the fluid handling system of FIG. 9A in a chemical blank load configuration, in accordance with an embodiment of this disclosure.

Referring to FIG. 9B, the fluid handling system 106 is shown in an example nozzle bypass configuration to send a chemical blank for analysis without passing the blank through the nozzle 304. In the nozzle bypass configuration, the pump 610 is in fluid communication with the holding loop 632 (e.g., with valve 630 in a second valve configuration) to push the fluid held in the holding loop 632 to a sample holding line (e.g., sample holding loop 634) via valve 636 in a first valve configuration and valve 638 in a first valve configuration. When the fluid is isolated in the sample holding loop 634, the fluid handling system 106 can switch configurations to a sample inject configuration to transfer the sample to an analytic system for analysis. The analytic system can include, but is not limited to, inductively coupled plasma spectrometry instrumentation for trace element composition determinations.

Figure 9C:
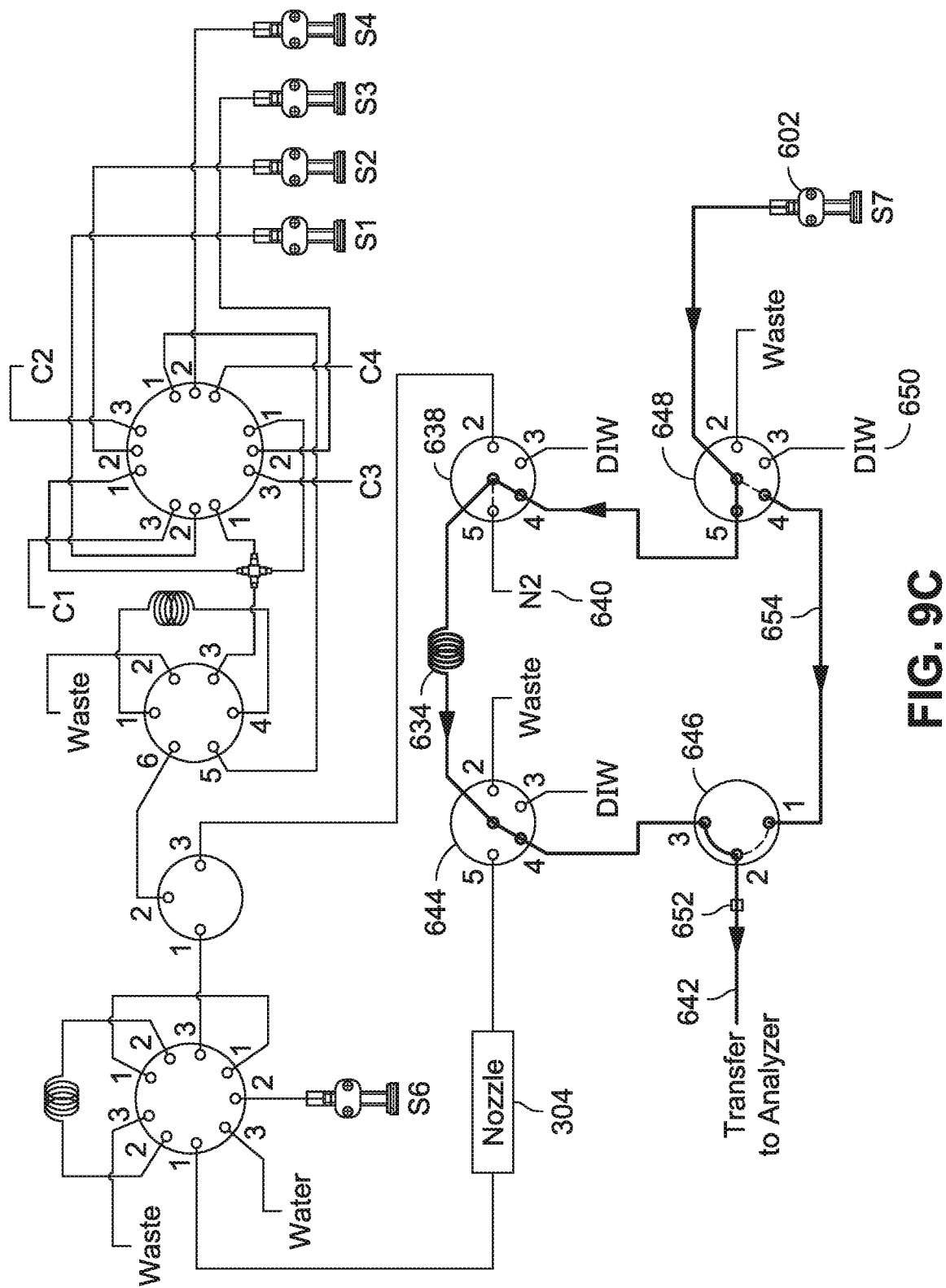
FIG. 9C is a schematic of the fluid handling system of FIG. 9A in a chemical inject configuration, in accordance with an embodiment of this disclosure.

Referring to FIG. 9C, the fluid handling system 106 is shown in an example chemical inject configuration, whereby the holding loop 632 is in fluid communication with one or more transfer mechanism. For example, in an implementation, the valve 638 is in a second configuration (shown dashed in FIG. 9C) to fluidically couple the holding loop 632 with a gas transfer source (e.g., nitrogen pressure source 640) to push the sample held in the holding loop 632 to a transfer line 642 to a sample analytic system via valve 644 in a first valve configuration and valve 646 in a first valve configuration. In an implementation, the valve 638 is in a third valve configuration (shown in FIG. 9C solid line) to fluidically couple the holding loop 632 with pump 602 via valve 648 in a first valve configuration (shown in FIG. 9C solid line) which pushes the sample held in the holding loop 632 to the transfer line 642 to the sample analytic system via valve 644 in the first valve configuration and valve 646 in the first valve configuration. The pump 602 can use a working solution (e.g., deionized water from DIW source 650) to push against the sample to the transfer line 642. In implementations, the fluid handling system 106 introduces a fluid gap between the working fluid and the sample, such as by introducing a bubble (e.g., from nitrogen pressure source 640) into the holding loop 632 prior to pushing of the working solution. In implementations, the fluid handling system 106 includes a sensor 652 adjacent the transfer line 642 to detect the presence or absence of a fluid in the transfer line 642. For example, the sensor 652 can detect the back end of the sample pushed from the holding loop 632 (e.g., by detecting a bubble in the line), where the sensor signal or lack thereof can inform a controller of the fluid handling system 106 to switch configurations of valve 646 and 648 to second valve configurations (shown dashed in FIG. 9C) to fluidically connect pump 602 with the transfer line 642 via fluid line 654. In such a configuration, the other portions of the fluid handling system 106 are isolated from the transfer of the sample to the sample analyzer to permit rinsing of those other portions during sample transfer.

Figure 9D:
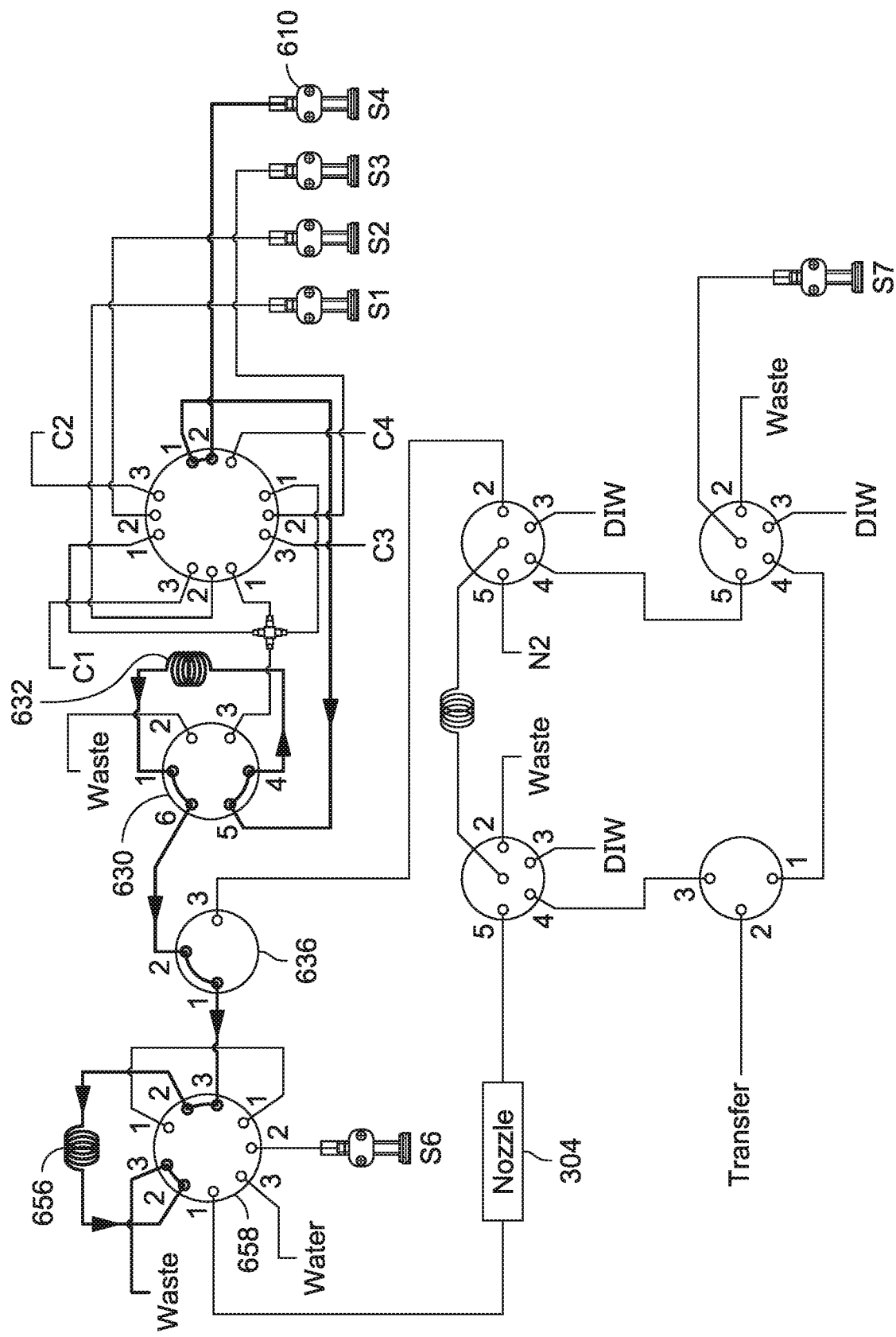
FIG. 9D is a schematic of the fluid handling system of FIG. 9A in a nozzle loop load configuration, in accordance with an embodiment of this disclosure.

Referring to FIG. 9D, the fluid handling system 106 is shown in an example nozzle loop load configuration, whereby the holding loop 632 is in fluid communication with a nozzle holding line (e.g., nozzle holding loop 656) to prepare to introduce the fluid to the nozzle 304. In the nozzle loop load configuration, the pump 610 is in fluid communication with the holding loop 632 (e.g., with valve 630 in the second valve configuration) to push the fluid held in the holding loop 632 to the nozzle holding loop 632 via valve 636 in a second valve configuration and valve 658 in a first valve configuration. In implementations, the nozzle holding loop 632 has a volume of approximately 500 µL, whereas the hold loop 632 has a volume of approximately 5-20 mL to permit fills of the nozzle holding loop 632 for each preparation of the scan solution through operation of the pumps 604, 606, 608. When the fluid is isolated in the nozzle holding loop 656, the fluid handling system 106 can switch configurations to a nozzle load configuration to transfer the fluid to the nozzle 304 for a scanning procedure of the wafer 108 or to take a nozzle blank sample (e.g., introduce the fluid to an inert surface, such as a surface of the rinse station 114, and remove the sample from the inert surface for analysis).

Figure 9E:
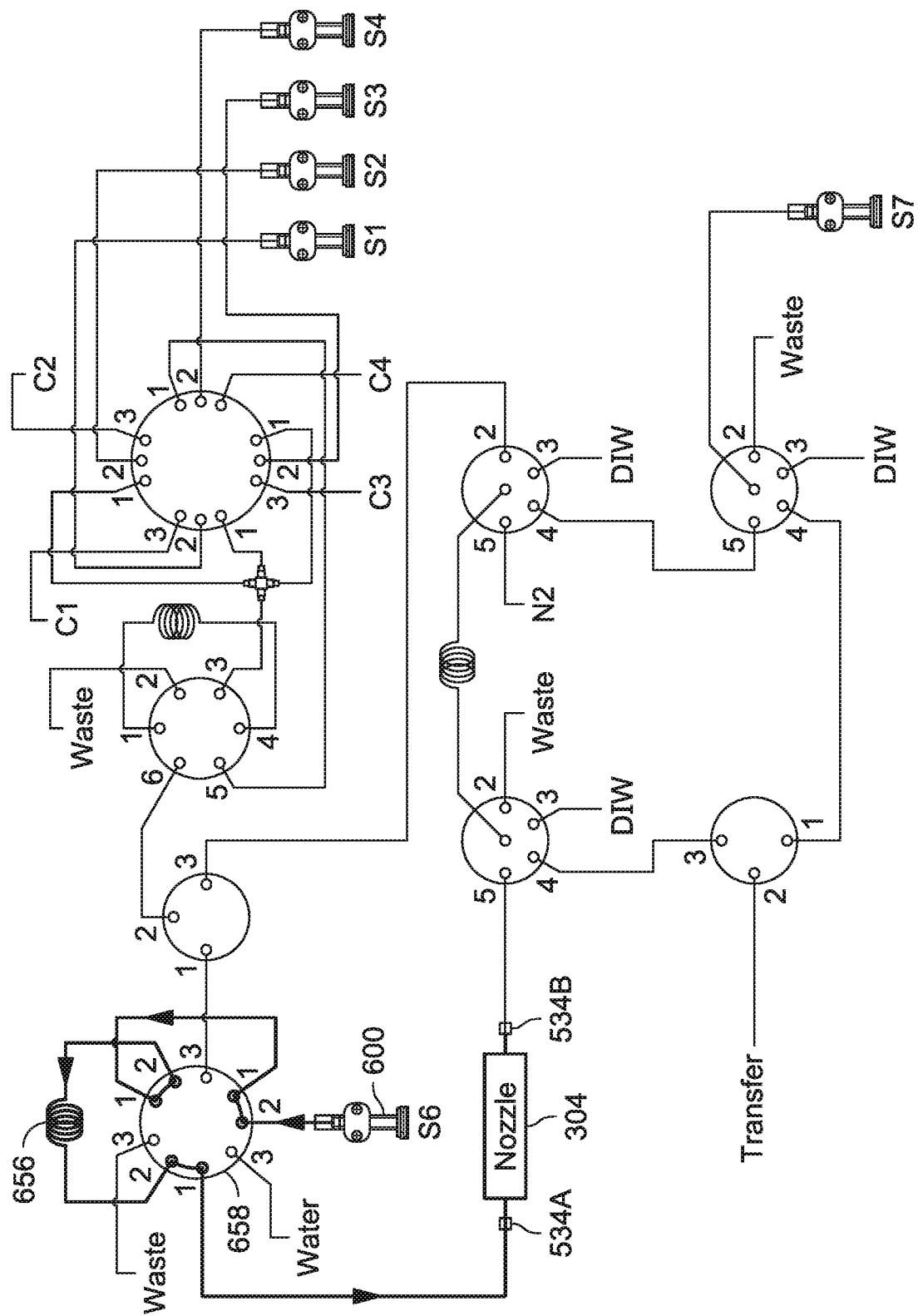
FIG. 9E is a schematic of the fluid handling system of FIG. 9A in a nozzle load configuration, in accordance with an embodiment of this disclosure.

Referring to FIG. 9E, the fluid handling system 106 is shown in an example nozzle load configuration, whereby the pump 600 is in fluid communication with the nozzle holding loop 656 and the nozzle 304 via valve 658 is a second valve configuration to push the fluid from the nozzle holding loop 656 to the nozzle 304. In implementations, during scanning procedures, the wafer 108 is held stationary while the nozzle 304 is loaded by the pump 600. In implementations, the system 100 performs a zeroing operation of the nozzle 304 (e.g., described with reference to FIGS. 8A through 8C) prior to filling of the nozzle 304 with the fluid. The nozzle is then placed in scan position over the wafer 108, where pump 600 can operate to push the fluid from the nozzle holding loop 656 to the inlet port 506 of the nozzle 304 through the nozzle body 500 to the first nozzle port 506 and onto the surface 146 of the wafer 108 (or onto the inert surface for nozzle blank analyses). In implementations, a controller of the fluid handling system 106 controls operation of the pump 600 based on sense signals or lack thereof from sensors 534A and 534B detecting the presence or lack thereof of fluid introduced to or fluid leaving the nozzle 304 indicating a filled nozzle 304. In implementations, the detection of the front end of the fluid by the sensor 534A causes the pump 600 to decrease the flow rate of the fluid introduced to the nozzle 304 (e.g., from an approximately 50 µL/min flow rate to a 10-20 µL/min flow rate). In implementations, the pump 600 operates to fill the nozzle 304 until the back end of the fluid is registered by the sensor 534B. The pump 600 can then operate for a time period to push the back end of the fluid into the nozzle 304, and then stops operation, whereby all the fluid previously held by the nozzle holding loop 656 is positioned on the surface 146 of the wafer 108 (or on the inert surface if a nozzle blank is being performed). The fluid is then supported on the surface 146 by the nozzle 304. In implementations, a portion of the fluid may protrude out from the nozzle hood 510, but can be maintained in contact with the remainder of the fluid within the channel 512, such as through adhesion forces. The system 100 then transitions to scanning the nozzle 304 over the surface 146 of the wafer 108. During the scanning procedure, the motor system 112 rotates the wafer 108 (e.g., at approximately 2 rpm), whereby the fluid supported by the nozzle 304 is transferred over the surface 146 of the wafer 108. In implementations, the fluid interacts with substantially the whole surface 146 of the wafer 108 in a single rotation of the wafer 108, however additional rotations can be performed. For example, the scanning procedure can involve two rotations of the wafer 108 by the motor system 112 to permit the fluid to contact the entire surface of the wafer 108 twice. Following scanning, the nozzle can be rotated to cause an end of the nozzle to extend over the edge of the wafer (e.g., as described with reference to FIG. 6), such as to assist in uptake of the fluid from the surface into the nozzle 304 via the second nozzle port 508.

Figure 9F:
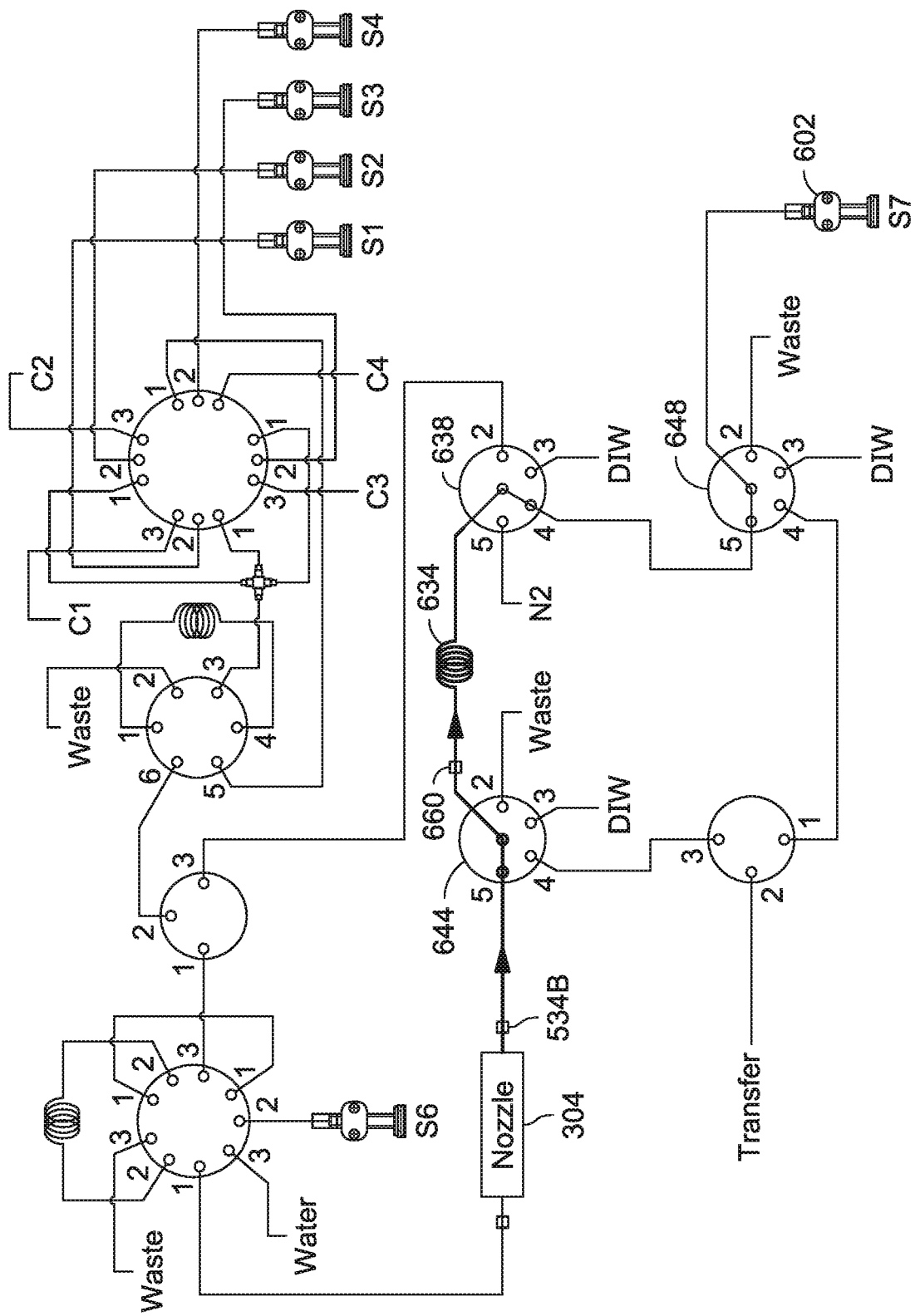
FIG. 9F is a schematic of the fluid handling system of FIG. 9A in a recovery configuration, in accordance with an embodiment of this disclosure.

Referring to FIG. 9F, the fluid handling system 106 is shown in an example recovery configuration, whereby the pump 602 is in fluid communication with the nozzle 304 via valve 648 in the first configuration, valve 638 in the third configuration, and valve 644 in a second configuration. In the recovery configuration, the pump 602 operates to draw the fluid from the surface 146 of the wafer 108 through the second nozzle port 508 and out the nozzle 304 via the outlet port 504, where the fluid is pulled into the sample holding loop 634. A sensor (e.g., sensor 660) can be utilized to control operation of the pump 602 similar to control of the pump 600 by output of the sensors 534A/534B. For example, sensor 660 can detect the back end of the fluid flowing into the sample holding loop 634 which can signal the pump 602 to stop operation (e.g., via a controller of the fluid handling system 106). Once the fluid is held in the sample holding loop 634, the fluid handling system 106 can transition to the chemical inject configuration, described with reference to FIG. 9C, to introduce the fluid to the sample analyzer via the transfer line 642. In implementations, the sample holding loop 634 has a larger volume (e.g., 1.5 mL) than the volume of the fluid provided to the nozzle 304 (e.g., 500 µL) to permit total recovery of the fluid following scanning.

Electromechanical devices (e.g., electrical motors, servos, actuators, or the like) may be coupled with or embedded within the components of the system 100 to facilitate automated operation via control logic embedded within or externally driving the system 100. The electromechanical devices can be configured to cause movement of devices and fluids according to various procedures, such as the procedures described herein. The system 100 may include or be controlled by a computing system having a processor or other controller configured to execute computer readable program instructions (i.e., the control logic) from a non-transitory carrier medium (e.g., storage medium such as a flash drive, hard disk drive, solid-state disk drive, SD card, optical disk, or the like). The computing system can be connected to various components of the system 100, either by direct connection, or through one or more network connections (e.g., local area networking (LAN), wireless area networking (WAN or WLAN), one or more hub connections (e.g., USB hubs), and so forth). For example, the computing system can be communicatively coupled to the chamber 102, the motor system 112, valves described herein, pumps described herein, other components described herein, components directing control thereof, or combinations thereof. The program instructions, when executed by the processor or other controller, can cause the computing system to control the system 100 (e.g., control pumps, selection valves, actuators, spray nozzles, positioning devices, etc.) according to one or more modes of operation, as described herein.

It should be recognized that the various functions, control operations, processing blocks, or steps described throughout the present disclosure may be carried out by any combination of hardware, software, or firmware. In some embodiments, various steps or functions are carried out by one or more of the following: electronic circuitry, logic gates, multiplexers, a programmable logic device, an application-specific integrated circuit (ASIC), a controller/microcontroller, or a computing system. A computing system may include, but is not limited to, a personal computing system, a mobile computing device, mainframe computing system, workstation, image computer, parallel processor, or any other device known in the art. In general, the term "computing system" is broadly defined to encompass any device having one or more processors or other controllers, which execute instructions from a carrier medium.

Program instructions implementing functions, control operations, processing blocks, or steps, such as those manifested by embodiments described herein, may be transmitted over or stored on carrier medium. The carrier medium may be a transmission medium, such as, but not limited to, a wire, cable, or wireless transmission link. The carrier medium may also include a non-transitory signal bearing medium or storage medium such as, but not limited to, a read-only memory, a random access memory, a magnetic or optical disk, a solid-state or flash memory device, or a magnetic tape.

Furthermore, it is to be understood that the invention is defined by the appended claims. Although embodiments of this invention have been illustrated, it is apparent that various modifications may be made by those skilled in the art without departing from the scope and spirit of the disclosure.

What is claimed is:

1. A nozzle system for scanning a surface of a material comprising:
    a nozzle including
        a nozzle body defining a first fluid port in fluid communication with a first nozzle port, and defining a second nozzle port in fluid communication with a second fluid port, the nozzle body configured to receive a fluid through the first fluid port and direct the fluid through the first nozzle port to introduce the fluid to a surface of a material, and
        a nozzle hood extending from the nozzle body adjacent the first nozzle port and the second nozzle port and defining a channel disposed between the first nozzle port and the second nozzle port, the nozzle hood configured to direct the fluid from the first nozzle port to the second nozzle port along the surface of the material; and
    a nozzle housing including
        a housing body defining an interior portion and an aperture through which at least a portion of the nozzle can pass when transitioning between an extended position and a retracted position.

2. The nozzle system of claim 1, wherein the nozzle housing further includes a sensor positioned at least partially within the interior portion, the sensor configured to measure the presence or absence of fluid passing through a fluid line coupled to the first fluid port or the second fluid port.

3. The nozzle system of claim 1, wherein the nozzle is moveably coupled to the nozzle housing via a coupler.

4. The nozzle system of claim 3, wherein the coupler defines an aperture, and wherein the nozzle housing includes a protrusion extending through the aperture.

5. The nozzle system of claim 4, wherein a top portion of the aperture rests on a portion of the protrusion when the nozzle is in the extended position.

6. The nozzle system of claim 4, wherein the nozzle housing further includes a lock structure configured to interact with the coupler to hold the nozzle in the retracted position.

7. The nozzle system of claim 6, wherein the lock structure includes an electromagnet.

8. The nozzle system of claim 6, wherein the protrusion does not support the aperture when the nozzle is in the retracted position.

9. The nozzle system of claim 1, wherein the channel is an elongated channel having opposing rounded ends defined by the nozzle hood.

10. The nozzle system of claim 9, wherein the first nozzle port is positioned tangent to an edge of a first rounded edge of the elongated channel, and wherein the second nozzle port is positioned at a center of a second rounded edge of the elongated channel distal to the first nozzle port.

11. The nozzle system of claim 1, wherein the channel has a length of approximately a radius of the surface of the material.

12. A nozzle for scanning a surface of a material comprising:
    a nozzle body defining a fluid port in fluid communication with a nozzle port, the nozzle body configured to receive a fluid through the fluid port and direct the fluid through the nozzle port to introduce the fluid to a surface of a material; and
    a nozzle hood extending from the nozzle body adjacent the nozzle port and configured to translate longitudinally across the surface of the material, the nozzle hood defining a channel disposed along a longitudinal portion of the nozzle hood at least partially between the nozzle port and an end of the longitudinal portion of the nozzle hood distal the nozzle port, the nozzle hood configured to direct the fluid from the nozzle port to the end of the longitudinal portion along the surface of the material.

13. The nozzle of claim 12, wherein the nozzle body includes opposing side walls, each of the opposing side walls including a tapered portion coupled to a vertical side wall.

14. The nozzle of claim 13, wherein each vertical side wall defines at least a portion of the nozzle hood.

15. The nozzle of claim 12, wherein the channel is an elongated channel having opposing rounded ends defined by the nozzle hood.

16. The nozzle of claim 15, wherein the nozzle port is positioned tangent to an edge of a first rounded edge of the elongated channel.

17. The nozzle of claim 12, wherein the channel has a length of approximately a radius of the surface of the material.

18. The nozzle of claim 12, wherein the channel has a volume of up to approximately 300 µL.

19. The nozzle of claim 12, wherein the nozzle body comprises at least one of chlorotrifluoroethylene (CTFE) or polytetrafluoroethylene (PTFE).

20. The nozzle of claim 12, wherein the material is a semiconducting wafer.

* * * * *